US009765327B2

(12) United States Patent
Slukvin et al.

(10) Patent No.: US 9,765,327 B2
(45) Date of Patent: Sep. 19, 2017

(54) INDUCTION OF HEMOGENIC ENDOTHELIUM FROM PLURIPOTENT STEM CELLS

(71) Applicant: Wisconsin Alumni Research Foundation, Madison, WI (US)

(72) Inventors: Igor Slukvin, Verona, WI (US); Irina Elcheva, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/183,191

(22) Filed: Jun. 15, 2016

(65) Prior Publication Data

US 2016/0355786 A1 Dec. 8, 2016

Related U.S. Application Data

(62) Division of application No. 14/058,959, filed on Oct. 21, 2013, now Pat. No. 9,382,531.

(60) Provisional application No. 61/716,875, filed on Oct. 22, 2012.

(51) Int. Cl.
| | |
|---|---|
| C12N 5/00 | (2006.01) |
| C12N 15/11 | (2006.01) |
| C12N 5/0789 | (2010.01) |
| C12N 15/00 | (2006.01) |
| C12N 15/66 | (2006.01) |

(52) U.S. Cl.
CPC ............ *C12N 15/11* (2013.01); *C12N 5/0647* (2013.01); *C12N 15/00* (2013.01); *C12N 15/66* (2013.01); *C12N 2501/60* (2013.01); *C12N 2501/998* (2013.01); *C12N 2506/02* (2013.01); *C12N 2506/45* (2013.01); *C12N 2510/00* (2013.01); *C12N 2740/16043* (2013.01)

(58) Field of Classification Search
CPC ................................ C12N 15/11; C12N 15/66
See application file for complete search history.

(56) References Cited

U.S. PATENT DOCUMENTS

| | | | |
|---|---|---|---|
| 5,652,122 A | 7/1997 | Barsoum et al. | |
| 5,674,980 A | 10/1997 | Barsoum et al. | |
| 6,051,427 A * | 4/2000 | Finer .................. | C07K 14/7051 435/320.1 |
| 6,153,745 A | 11/2000 | Brown et al. | |
| 6,521,453 B1 | 2/2003 | Crameri et al. | |
| 6,841,535 B2 | 1/2005 | Divita et al. | |
| 6,881,825 B1 | 4/2005 | Robbins et al. | |
| 7,964,196 B2 | 6/2011 | del los Rios et al. | |
| 8,546,140 B2 | 10/2013 | Mack et al. | |
| 9,382,531 B2 | 7/2016 | Slukvin et al. | |

| | | | |
|---|---|---|---|
| 2012/0046346 A1 | 2/2012 | Rossi et al. | |
| 2014/0037600 A1 | 2/2014 | Yu et al. | |
| 2014/0045265 A1* | 2/2014 | Belmonte ............ | C12N 5/0647 435/377 |

OTHER PUBLICATIONS

Altschul, et al. "Gapped BLAST and PSI-BLAST: a new generation of protein database search programs." Nucleic acids research 25.17 (1997): 3389-3402.
Baltzinger, et al. "XI erg: expression pattern and overexpression during development plead for a role in endothelial cell differentiation", Developmental dynamics, 1999, 216:420-33.
Barnes, et al., "Analysis of the Hand1 cell lineage reveals novel contributions to cardiovascular, neural crest, extra-embryonic, and lateral mesoderm derivatives," Developmental dynamics, 2010, 239:3086-97.
Becker-Hapak, M. and Dowdy, S. "Protein Transduction: Generation of Full-Length Transducible Proteins Using the TAT System," (2003) Curr Protocols in Cell Biol, Unit 20.2; doi:10.1002/0471143030.cb2002s18; John Wiley & Sons, Inc.
Blobel et al. "Rescue of GATA-1-deficient embryonic stem cells by heterologous GATA-binding proteins." Molecular and Cellular Biology 15.2 (1995): 626-633.
Boisset, et al., "In vivo imaging of haematopoietic cells emerging from the mouse aortic endothelium," 2010, Nature 464:116-20.
Chen, et al. "Erythroid/myeloid progenitors and hematopoietic stem cells originate from distinct populations of endothelial cells," 2011 Cell Stem Cell 9:541-52.
Choi, et al. "Identification of the hemogenic endothelial progenitor and its direct precursor in human pluripotent stem cell differentiation cultures" 2012 Cell Reports 2:553-67.
Davidson, et al. "Emerging properties of animal gene regulatory networks," 2010 Nature 468:911-20.
Donaldson, et al. "Genome-wide identification of cis-regulatory sequences controlling blood and endothelial development," 2005 Hum Mol Genet 14:595-601. Epub Jan. 13, 2005.
Ferrer-Costa, et al. "PMUT: a web-based tool for the annotation of pathological mutations on proteins," 2005, Bioinformatics, 21(14), 3176-3178.
Gekas, et al. "The placenta is a niche for hematopoietic stem cells," 2005 Dev Cell 8:365-75.
Godin, et al. "The hare and the tortoise: an embryonic haematopoietic race," 2002 Nat Rev Immunol 2:593-604.
Henikoff et al. "Amino acid substitution matrices from protein blocks." Proceedings of the National Academy of Sciences 89.22 (1992): 10915-10919.
Hromas, et al. "Cloning and characterization of exodus, a novel β-chemokine," 1997, Blood, 89(9), 3315-3322.
Jaffredo, et al. "Tracing the progeny of the aortic hemangioblast in the avian embryo," 2000 Dev Biol 224:204-14.
Klug, et al, "The Discovery of Zinc Fingers and Their Development for Practical Applications in Gene Regulation and Genome Manipulation." (2010) Q Rev Biophys.; Feb;43(1):1-21; doi:10.1017/S0033583510000089.

(Continued)

*Primary Examiner* — Marcia S Noble
(74) *Attorney, Agent, or Firm* — Quarles & Brady, LLP

(57) ABSTRACT

Described herein are methods and related compositions for inducing differentiation of human pluripotent stem cells (hPSCs) into hemogenic endothelium with pan-myeloid potential or restricted potential, by forced expression in the hPSCs of a combination of transcription factors as described herein.

21 Claims, 12 Drawing Sheets

(56) References Cited

OTHER PUBLICATIONS

Kopsidas et al., "RNA Mutagenesis Yields Highly Diverse mRNA Libraries for in vitro Protein Evolution." (2007) BMC Biotechnology, 7:18-29.
Lee, et al. "The Er71 is an important regulator of hematopoietic stem cells in adult mice," 2011 Stem Cells 29:539-48.
Lessard, et al. "Genetic programs regulating HSC specification, maintenance and expansion," 2004 Oncogene 23:7199-209.
Li, et al. "Endothelial cells in the early murine yolk sac give rise to CD41-expressing hematopoietic cells," 2005 Stem Cells Dev 14:44-54.
Li, et al. "Mouse embryonic head as a site for hematopoietic stem cell development," 2012 Cell Stem Cell 11:663-75.
Mahlapuu, et al. "The forkhead transcription factor Foxf1 is required for differentiation of extra-embryonic and lateral plate mesoderm." 2001 Development 128:155-66.
Martinez-Salas "Internal Ribosome Entry Site Biology and its Use in Expression Vectors." (1999) Curr Opin Biotechnol 10(5):458-464.
Meadows, et al. "Regulation of endothelial cell development by ETS transcription factors," 2011 Seminars in cell & developmental biology 22:976-84.
Nakano, et al. "Haemogenic endocardium contributes to transient definitive haematopoiesis," 2013 Nature communications 4:1564.
Neuhaus, et al. "Xenopus er71 is involved in vascular development," 2010 Developmental dynamics 239:3436-45.
Osuna, et al. Nucleic Acids Research, 2004, 32(17), e136.
Piechaczek et al "A Vector based on the SV40 origin of Replication and Chromosomal S/MARs Replicates Episomally in CHO Cells." (1999) Nucleic Acids Res, 27:426-428.
Pimanda, et al. "Gata2, Fli1, and Scl form a recursively wired gene-regulatory circuit during early hematopoietic development," 2007 Proc Natl Acad Sci U S A 104:17692-7. Epub Oct. 25, 2007.
Ren, et al. "Scl isoforms act downstream of etsrp to specify angioblasts and definitive hematopoietic stem cells," 2010 Blood 115:5338-46.
Robb, et al. "The scl gene product is required for the generation of all hematopoietic lineages in the adult mouse," 1996 EMBO J 15:4123-9.
Taoudi, et al. "Functional identification of the hematopoietic stem cell niche in the ventral domain of the embryonic dorsal aorta," 2007 Proc Natl Acad Sci U S A 104:9399-403..
Teitell, et al. "Transcriptional activators, repressors, and epigenetic modifiers controlling hematopoietic stem cell development," 2006 Pediatric research 59:33R-9R.
Trichas et al. "Use of the Viral 2A Peptide for Bicistronic Expression in Transgenic Mice." (2008), BMC Biol. 6:40.
Wilson et al, "Design and Development of Artificial Zinc Finger Transcription Factors and Zinc Finger Nucleases to the h TERT Locus" (2013) Mol Ther Neucleic Acids 2,e87; doi:10.1038 (published online).
Wilson, et al. "Transcriptional regulation of haematopoietic transcription factors," 2011 Stem cell research & therapy 2:6.
Wilson, et al. "The transcriptional program controlled by the stem cell leukemia gene Scl/Tal1 during early embryonic hematopoietic development," 2009 Blood 113:5456-65.
Wong, et al. "Sequence saturation mutagenesis (SeSaM): a novel method for directed evolution," Nucleic Acids Research, 2004, 32(2), e26.
Vodyanik, et al. "A mesoderm-derived precursor for mesenchymal stem and endothelial cells," 2010 Cell Stem Cell 7:718-29.
Visvader, et al. "Unsuspected role for the T-cell leukemia protein SCL/tal-1 in vascular development," 1998 Genes Dev 12:473-9.
Wong, et al. "Identification of vasculature-specific genes by microarray analysis of Etsrp/Etv2 overexpressing zebrafish embryos," 2009 Developmental dynamics 238:1836-50.
Xu, et al. "Random mutagenesis libraries: Optimization and simplification by PCR," BioTechniques, 1999, 27, 1102-1108.
Yates et al "A cis-acting element from the Epstein-Barr viral genome that permits stable replication of recombinant plasmids in latently infected cells." (1984) Proc Natl Acad. Sci. USA, 81:3806-3810.
Yokomizo, et al. "Three-dimensional cartography of hematopoietic clusters in the vasculature of whole mouse embryos," 2010 Development 137:3651-61.
Yusa, K. et al. "A Hyperactive PiggyBac Transposase for Mammalian Applications." (2011) Proc Natl Acad Sci USA, 108:1531-1536 doi:10.1073/pnas.1008322108.
Zovein, et al. "Fate tracing reveals the endothelial origin of hematopoietic stem cells," 2008 Cell Stem Cell 3:625-36.

* cited by examiner

INDUCTION OF HEMOGENIC ENDOTHELIUM FROM PLURIPOTENT STEM CELLS

CROSS-REFERENCE TO RELATED APPLICATIONS

This application is a divisional of U.S. application Ser. No. 14/058,959 filed Oct. 21, 2013, which claims priority to U.S. Application 61/716,875 filed Oct. 22, 2012, all of which are incorporated herein by reference for all purposes.

STATEMENT REGARDING FEDERALLY SPONSORED RESEARCH OR DEVELOPMENT

This invention was made with government support under HL099773 awarded by the National Institutes of Health. The government has certain rights in the invention.

BACKGROUND

Human pluripotent stem cells (hPSCs), including embryonic stem cells (hESCs) and induced PSCs (hiPSCs) offer a potentially plentiful source of blood cells for experimentation and therapeutic purposes. Significant advances have been made in hematopoietic differentiation from hPSCs based on the use of specific culture conditions designed to mimic developmental processes. However, the identification of key transcriptional regulators of hematopoietic commitment, and their overexpression would enable the directed and scaled conversion of human pluripotent stem cells to hematopoietic stem cells (HSCs) and related blood cells.

SUMMARY

Described herein are methods and related compositions for generating human hemogenic endothelial cells with pan-myeloid potential by forced expression, in human pluripotent stem cells, of combinations of transcription factors as disclosed herein. Also described are methods and related compositions for generating human endothelial cells with restricted erythroid, megakaryotic, and macrophage potential by forced expression, in human pluripotent stem cells, of combinations of transcription factors as disclosed herein.

Accordingly, in a first aspect provided herein is a method for generating human hemogenic endothelial cells with pan-myeloid potential, comprising the steps of: (i) forcing expression, in human pluripotent stem cells, of one of the following protein combinations: (a) an ETV2 or ERG protein and a GATA1 protein, or functional homologs thereof; (b) an ETV2 or ERG protein and a GATA2 protein, or functional homologs thereof; or (c) an ETV2 or ERG protein and a GFI 1 protein, or functional homologs thereof; and step (ii) culturing the human pluripotent stem cells following step (i), under culture conditions that support expansion of hematopoietic cells, to obtain hemogenic endothelial cells that are VE-cadherin$^+$, CD226$^+$, and CD73$^-$.

In some embodiments, the method further comprises culturing the hemogenic endothelial cells of step (ii) for an additional period of at least one to about four days to obtain CD43$^+$ hematopoietic cells.

In some embodiments the culturing conditions of step (ii) include culturing in the presence of FGF2, SCF, and thrombopoietin.

In some embodiments the forced expression lasts at least two to about three days.

In some embodiments the forced expression in step (i) includes transduction of human pluripotent stem cells with a recombinant expression virus, transfection with a double-stranded DNA expression vector; transfection with a modified mRNA; protein transduction; or a combination thereof.

In some embodiments the ETV2 protein, ERG protein, GATA1 protein, or GATA2 protein, or GFI1 protein are from human, mouse, or rat.

In some embodiments the functional homologs are polypeptides selected from the group consisting of: (i) a polypeptide comprising an amino acid sequence at least 90% identical to an ETV2, GATA1, ERG, GFI1, or GATA2 protein from human, mouse, or rat, wherein the polypeptide transactivates one or more target genes transactivated by the ETV2, GATA1, or GATA2 proteins in human pluripotent stem cells; and (ii) a fusion polypeptide comprising an amino acid sequence that is at least 90% identical to the amino acid sequence of (a) a DNA binding domain of human, mouse, or rat ETV2, GATA1, ERG, GFI1, or GATA2 and (b) a heterologous transactivator domain; wherein the fusion polypeptide transactivates one or more target genes transactivated by human, mouse, or rat ETV2, GATA1, ERG, GFI1, or GATA2 proteins in human pluripotent stem cells. In some embodiments the functional homologs comprise the amino acid sequence of human, mouse, or rat ETV2, GATA1, ERG, GFI1, or GATA2.

In another aspect disclosed herein is a method for generating human hemogenic endothelial cells with restricted erythroid, megakaryocytic, and macrophage potential. The method includes the steps of: (i) forcing expression, in human pluripotent stem cells, of a TAL1 protein and a GATA2 protein or GATA1 protein or functional homologs thereof; and (ii) culturing the human pluripotent stem cells following step (i), under culture conditions that support expansion of hematopoietic cells, to obtain hemogenic endothelial cells that are VE-cadherin$^+$, CD226$^+$, CD73$^-$, and have restricted erythroid, megakaryocytic, and macrophage potential, wherein the forced expression.

In some embodiments, the forced expression in this method does not include forced expression of LMO2.

In some embodiments the above method further includes culturing the hemogenic endothelial cells (with restricted erythroid, megakaryocytic, and macrophage potential) for an additional period to obtain erythrocytes, megakaryocytes, or macrophages.

In some embodiments the method further comprises forcing the expression of LMO2 or a functional homolog thereof in the human pluripotent stem cells.

In a further aspect described herein is a recombinant human pluripotent stem cell comprising: (i) one or more exogenous nucleic acids suitable for expression of (a) an ETV2 or ERG protein, and a GATA1 protein, or functional homologs thereof; (b) an ETV2 or ERG protein, and a GATA2 protein, or functional homologs thereof; or (c) an ETV2 or ERG protein, and a GFI1 protein (ii) exogenous polypeptides comprising the amino acid sequences of any of (a), (b), or (c).

In some embodiments the exogenous polypeptides comprise the amino acid sequence of a protein transduction domain.

In some embodiments the recombinant human pluripotent stem cell is integration free. In some embodiments, exogenous nucleic acids in the integration-free human pluripotent stem cell are episomal expression vectors. In other embodiments, the exogenous nucleic acids in the integration-free recombinant human pluripotent stem cells are modified mRNAs.

In a related aspect described herein is a cell culture composition for generating human hemogenic endothelial cells with pan-myeloid potential, comprising any of the above-mentioned recombinant human pluripotent stem cells and a cell culture medium suitable for expansion of hematopoietic cells. In some embodiments the suitable cell culture medium includes FGF2, SCF, and thrombopoietin.

In yet another aspect described herein is a kit for hemogenic reprogramming that includes: (i) one or more isolated nucleic acids comprising an open reading frame for (a) ETV2 or ERG, and GATA1; (b) ETV2 or ERG, and GATA2; (c) ETV2 or ERG, and GFI1; or (c) TAL1 and GATA2; or (ii) one or more recombinant expression viruses suitable for expression, in human pluripotent stem cells, of (a) ETV2 or ERG, and GATA1; (b) ETV2 or ERG, and GATA2; (c) ETV2 or ERG, and GFI1; or (c) TAL1 and GATA2.

In some embodiments the one or more isolated nucleic acids in the kit are modified mRNAs.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
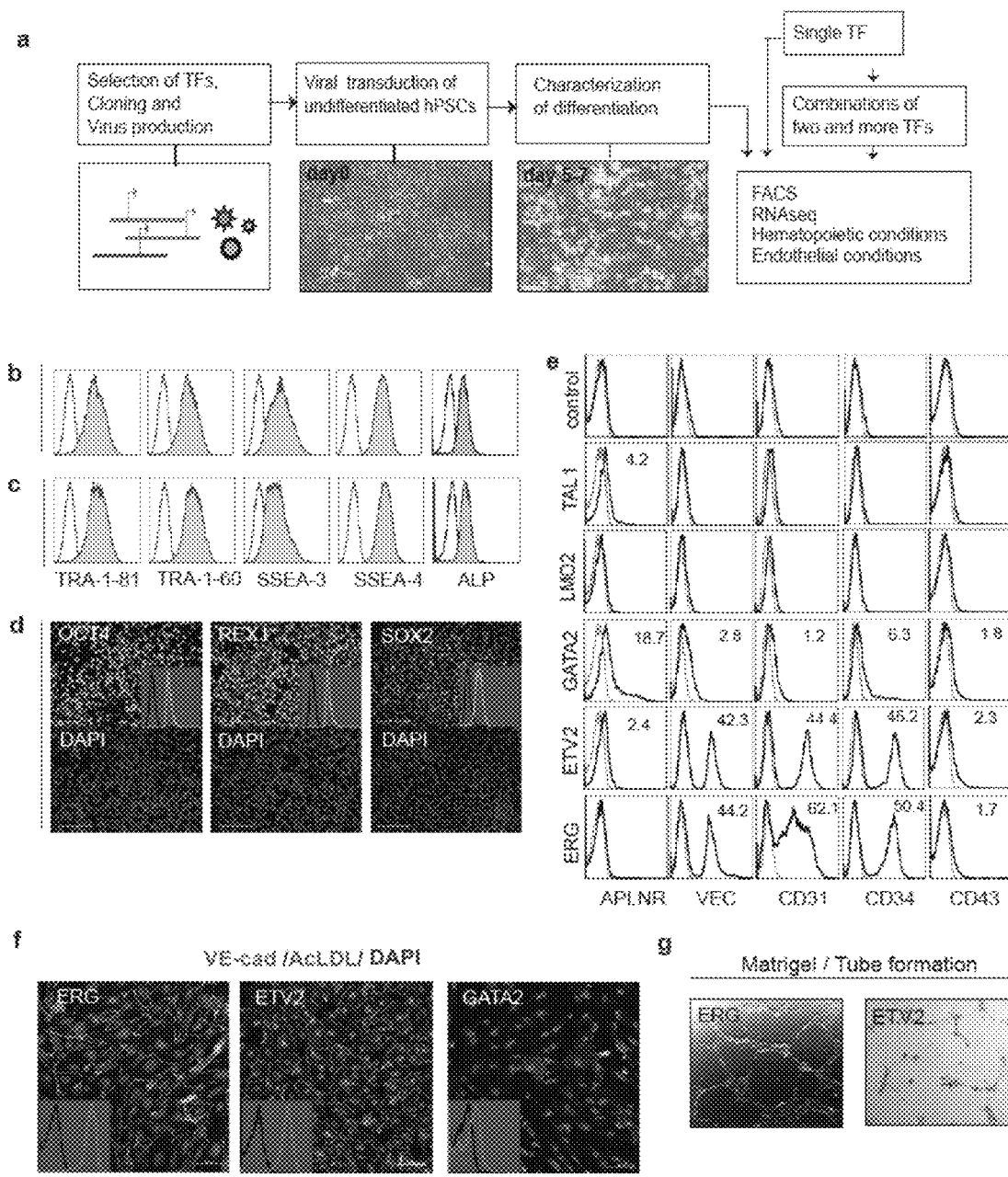
FIG. 1 Gain-of-function screening in hPSCs. (a) Schematic diagram of screening system; (b-d) Expression of pluripotency markers in H1 hESCs growing on Matrigel™ for 5 days in standard conditions TeSR1™ medium (b) and TeSR1™ medium containing SCF (100 ng/ml) TPO (50 ng/ml) and bFGF (20 ng/ml) (c and d); (e) Flow cytometric analysis of mesodermal, endothelial and hematopoietic markers in control hESCs and hESCs transduced with indicated TFs on day 5 post-transduction; (f-g) ETV2- and ERG-transduced cells acquire endothelial characteristics as shown by positive VE-cadherin immunostaining, AcLDL uptake (f) and formation of endothelial tubes in solidified Matrigel™ in the presence of VEGF (g). Scale bar, d, f, g, 100 µm.

Advancing pluripotent stem cell technologies for modeling HSC development and therapies requires identification of the key regulator of hematopoietic commitment from human pluripotent stem cells (hPSCs). Transcription factors (TFs) have been recognized as critical controllers of early embryonic development. The factors are thought to function as key elements of the gene regulatory network that guide the acquisition of specific properties by particular cell type. To define the key TFs required for induction of blood, we performed gain-of-function genetic screens in human embryonic stem cells (hESCs) to identify specific combinations of TFs that induced differentiation of hPSCs into human hemogenic endothelial cells with pan-myeloid potential. In some cases the identified combination of transcription factors induced differentiation of hPSCs into hemogenic endothelial cells with restricted erythroid, megakaryocytic, and macrophage potential. The identified transcription factors are referred to as "induction factors," (IFs) herein.

I. Definitions

"Forced Expression" refers to inducing an increase in the level of a protein of interest (e.g., a transcription factor) in a population of host cells, e.g., hPSCs. Forced expression can include one or more of the following in any combination: introducing exogenous nucleic acids encoding the protein of interest (e.g., by viral transduction, plasmid expression vector transfection, or modified mRNA transfection); protein transduction; genomic modification of a host cell, e.g., replacing a promoter to increase the expression of an endogenous (native) gene; and contacting host cells with a small molecule that induces increased expression of an endogenous protein.

"Functional Homolog" refers to an induction factor that transactivates at least some of the same promoters or target genes as the reference induction factor. In some cases, the functional homolog transactivates a cognate promoter of induction factor with at least 10% to 95% of the corresponding activity, e.g., 15%, 20%, 30%, 40%, 50%, 60%, 70%, 80%, 90%, or another level of transactivation activity of the reference induction factor from at least 10% to 95%. A functional homolog can also be a paralog, i.e., a naturally occurring protein having at least 80% to 99% amino acid sequence identity to the reference induction factor, similar function, and belonging to the same protein family.

"Integration-Free" refers to the absence of exogenous sequences in a genome;

"Induction Factor" refers to a protein the forced expression of which drives differentiation of host cells (e.g., hPSCs) into hemogenic endothelial cells.

"Recombinant Expression Virus" refers to a virus comprising a protein capsid and a genome that includes an expression cassette suitable for expression in a mammalian host cell.

"Recombinant Human Pluripotent Stem Cell" refers to an hPSC (e.g., an hiPSC or hESC) that comprises either an exogenous nucleic acid encoding a polypeptide (e.g., an expression vector or a modified mRNA), or an exogenous polypeptide.

II. Methods

Generation of Hemogenic Endothelial Cells

In some embodiments described herein is a method for generating human hemogenic endothelial cells with pan-myeloid potential, comprising forcing expression in hPSCs of one of the combinations of IFs described below; and, afterwards, culturing the human pluripotent stem cells under culture conditions that support expansion of hematopoietic cells to obtain hemogenic endothelial cells that are VE-cadherin$^+$, CD226$^+$, and CD73$^-$.

Prior to forced expression hPSCs are grown by any of a number of known methods in the art, although, preferably, the hPSCs are grown for at least two passages, prior to forced expression, under feeder-free conditions, e.g., in TeSR™ or E8™ culture medium in combination with an extracellular matrix substrate such as Matrigel™ or vitronectin.

Forced expression of a combination of IFs, or functional homologs thereof, is then carried out by any of a number of methods described herein to obtain human hemogenic endothelial cells with pan-myeloid potential, or, in other embodiments, to obtain human hemogenic endothelial cells with restricted potential.

After initiating forced expression of IFs in the hPSCs, these cells are cultured for a period of about 24 hours in a medium suitable for culture of hPSCs, e.g., complete TeSR1™ medium on an extracellular matrix substrate (e.g., Matrigel™), after which the medium is replaced with growth factor-free TeSR1™ base medium supplemented with stem cell factor (SCF; 10-200 ng/ml); thrombopoietin (TPO; 10-200 ng/ml) and FGF2 (10-100 ng/ml), and the cells are cultured for up to seven days, after which cells can be cultured in complete StemSpan™ SFEM medium (Stem-Cell Technologies, Vancouver) or StemLine® HSC medium prior to identification of differentiated cells. In some embodiments, the forced expression culture period is for at least two to about three days. In some embodiments the forced expression culture period is for about two to about seven days prior to analysis of differentiation.

The resulting human hemogenic endothelial cells are identified as VE-cadherin$^+$, CD226$^+$, and CD73$^-$ cells. In some embodiments, the hemogenic endothelial cells are isolated by cell sorting to initiate clonogenic cultures in the presence of OP9 stromal cells, to generate colonies of CD43$^+$ hematopoietic cells with multilineage colony forming cell (CFC) potential. In some embodiments, the CD43$^+$ cells generated from hemogenic endothelium subjected to colony-forming assay in serum-containing methylcellulose medium (e.g., MethoCult™, Stem Cell Technologies) supplemented with SCF, G-CSF, GM-CSF, IL3, IL6, and EPO. In some embodiments, colony-forming cells expanded in cultures containing TeSR1™ or aMEM medium with 30% FBS and hematopoietic cytokines (SCF—100 ng/ml, IL3—10 ng/ml, IL6—20 ng/ml, GM-CSF—10 ng/ml, G-CSF—20 ng/ml, EPO—3 u/ml) or SFEM medium supplemented with SCF-100 ng/ml, TPO 50 ng/ml and FGF2 20 ng/ml. The expansion cultures can then be assessed for various types of myeloid cells. Cultures with pan-myeloid potential give rise to CD34$^+$CD117$^+$ primitive progenitors, CD163$^+$ macrophages, CD66b$^+$ granulocytes, CD41a$^+$ megakaryocytic and CD235a$^+$ erythroid cells. Cultures with restricted myeloid potential, generated as described herein, generate almost exclusively CD235a$^+$ erythroid and CD41a$^+$ megakaryocytic cells. Cell surface characterization of, or isolation of cells obtained by the above-described methods can be performed by a number of methods known in the art including, but not limited to, flow cytometry, magnetic-activated cell sorting (MACS), and acoustic cell sorting.

Induction Factors

Suitable combinations of IFs to obtain human hemogenic endothelial cells with pan-myeloid potential include any of those listed in Table 1:

TABLE 1

IF Combinations to Induce Human Hemogenic Endothelial Cells with Pan-Myeloid Potential from hPSCs

| Combination | IFs |
|---|---|
| I | ETV2 (SEQ ID NO: 1) and GATA1 (SEQ ID NO: 2) |
| II | ERG (SEQ ID NO: 3) and GATA1 (SEQ ID NO: 2) |
| III | ETV2 (SEQ ID NO: 1) and GATA2 (SEQ ID NO: 4) |
| IV | ERG (SEQ ID NO: 3) and GATA2 (SEQ ID NO: 4) |
| V | ETV2 (SEQ ID NO: 1) and GFI1 (SEQ ID NO: 5) |
| VI | ERG (SEQ ID NO: 3) and GFI1 (SEQ ID NO: 5) |

Suitable combinations of IFs to obtain human hemogenic endothelial cells with restricted erythroid, megakaryocytic, and macrophage potential include any of those listed in Table 2:

TABLE 2

IF Combinations to Induce Human Hemogenic Endothelial Cells and Blood Cells with Restricted Potential from hPSCs

| Combination | IFs |
|---|---|
| I-R | TAL1 (SEQ ID NO: 6) and GATA1 (SEQ ID NO: 2) |
| II-R | TAL1 (SEQ ID NO: 6) and GATA2 (SEQ ID NO: 4) |
| III-R | TAL1 (SEQ ID NO: 6) and GATA1 (SEQ ID NO: 2) and LMO2 (SEQ ID NO: 7) |
| IV-R | TAL1 (SEQ ID NO: 6) and GATA2 (SEQ ID NO: 4) and LMO2 (SEQ ID NO: 7) |

In some embodiments, the combinations of IFs used to induce differentiation of hPSCs into hemogenic endothelial cells with restricted potential do not include LMO2. Preferably, the IFs listed in Tables 1 and 2 correspond to the human homologs of these proteins, however, in other embodiments, one or more of the IFs are mouse or rat homologs.

In other embodiments one or more of the listed IFs to be used in the methods described herein are functional homologs of IFs listed in Tables 1 and 2.

In some embodiments one or more of the IFs listed in Table 1 or Table 2 is replaced with a functional homolog. A functional homolog, in the case of a transcription factor, refers to a transcription factor that transactivates at least some of the same promoters or target genes as the reference IF. In some cases, the functional homolog transactivates a cognate promoter of one the above-mentioned IFs with at least 10% to 95% of the corresponding activity, e.g., 15%, 20%, 30%, 40%, 50%, 60%, 70%, 80%, 90%, or another level of transactivation activity of the reference IF from at least 10% to 95%. Methods for measuring transactivation activity are well known in the art and include, but are not limited to, promoter-reporter activity assays (e.g., promoter-luciferase assays) and the like. In some embodiments, the functional homolog is a paralog, i.e., a naturally occurring protein having at least 80% to 99% amino acid sequence identity (e.g., 85%, 90%, 92%, 94%, 95%, 97%, or another percent identity) to the reference IF, similar function, and belonging to the same protein family.

In some embodiments an IF functional homolog is a polypeptide comprising an amino acid sequence at least 90%, e.g., identical to an ETV2, ERG, GATA1, GATA2, GFI1, or TAL1 protein from human, mouse, or rat, where the polypeptide transactivates one or more cognate target genes of the foregoing IFs.

In some embodiments, the DBD amino acid sequence of one of the IFs to be used is at least 85% to 100% identical to the DBD sequence of the DBD amino acid sequence of a mouse, rat, human, or chicken homolog of one of the IFs listed in Table 1 or Table 2, e.g., at least 90%, 92%, 93%, 95%, 97%, 99%, or another percent amino acid identity from at least 85% to 100% identical. In other embodiments, the functional homolog DBD, contains up to 10 amino acid changes (i.e., deletions, insertions, or substitutions), i.e., 0, 1, 2, 3, 4, 5, 6, 7, 8, 9, or 10 amino acid changes in the amino acid sequence of the DBD.

The skilled artisan also recognizes that transcription factors often contain discrete DNA binding domains (DBDs) and transactivation domains (TDs), and in many cases it is possible to substitute a native transactivation domain with an unrelated transactivation domain (e.g., VP16, GAL4, or LEX TDs) well known in the art and often used to generate functional heterologous transcription factors having a desired DBD, e.g., the GATA2 DBD, and a heterologous TD, e.g. GATA1(DBD)-VP16, as exemplified in Blobel et at (1995), *Mol Cell Biol,* 15(2):626-633. The amino acid sequence of the VP16 transactivation domain (SEQ ID NO:13) is provided below:

```
                                             (SEQ ID NO: 13)
TKTLMKKDKYTLPGGLLAPGGNSMASGVGVGAGLGAGVNQRMDSYA

HMNGWSNGSYSMMQDQLGYPQHSTTAPITDVSLGDELRLDGEEVDM

TPADALDDFDLEMLGDVESPSPGMTHDPVSYGALDVDDFEFEQMFT

DALGIDDFGG
```

In yet other embodiments a functional homolog may comprise the amino acid sequence of an artificial transcription factor that has no significant sequence identity to any of the reference IF sequences (SEQ ID NOs:1-7), but is able to bind and transactivate a cognate promoter sequence. For example, the artificial DBD may be generated by designing zinc finger-containing proteins having binding specificity for a designed target sequence (e.g., a GATA motif). The zinc-finger DBD is then fused to a transactivator protein, e.g., VP16 to generate a fusion protein that is an artificial TF. See, e.g., Wilson et al (2013), *Mol Ther Nucleic Acids,* (published online): 2, e87; doi:10.1038; and Klug (2010), *Q Rev Biophys.*; February; 43(1):1-21. doi: 10.1017/S0033583510000089.

Evaluating the structural and functional homology of two or more polypeptides generally includes determining the percent identity of their amino acid sequences to each other. Sequence identity between two or more amino acid sequences is determined by conventional methods. See, for example, Altschul et al., (1997), Nucleic Acids Research, 25(17):3389-3402; and Henikoff and Henikoff (1982), Proc. Natl. Acad. Sci. USA, 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the shorter sequence plus the number of gaps introduced into the longer sequence in order to align the two sequences])(100).

Those skilled in the art will appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman (1988), Proc. Nat'l Acad. Sci. USA, 85:2444, and by Pearson (1990), Meth. Enzymol., 183:63. Briefly, FASTA first characterizes sequence similarity by identifying regions shared by the query sequence (e.g., any of SEQ ID NOs:1-7) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps.

Finally, the highest scoring regions of the two amino acid sequences are aligned using a modification of the Needleman-Wunsch-Sellers algorithm (Needleman and Wunsch (1970), J. Mol. Biol., 48:444-453; Sellers (1974), SIAM J. Appl. Math., 26:787), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson (1990), Meth. Enzymol., 183:63.

A number of considerations are useful to the skilled artisan in determining if a particular amino acid sequence variant of one of the IFs described herein is likely to have suitable transcriptional activity compared to an IF comprising a naturally occurring IF reference amino acid sequence (e.g., ETV2 (SEQ ID NO:1). These considerations include, but are not limited to: (1) known structure-function relationships for the variant polypeptide, e.g., the presence of discrete functional domains, e.g., a DBD; and (2) the presence of amino acid sequence conservation among naturally occurring homologs (e.g., in paralogs and orthologs) of an IF, as revealed by sequence alignment algorithms as described herein. Notably, a number of bioinformatic algorithms are known in the art that successfully predict the functional effect, i.e., "tolerance" of particular amino substitutions in the amino acid sequence of a protein on its function. Such algorithms include, e.g., pMUT, SIFT, PolyPhen, and SNPs3D. For a review see, e.g., Ng and Henikoff (2006), Ann Rev Genomics Hum Genet., 7:61-80. For example, pMUT predicts with a high degree of accuracy (about 84% overall) whether a particular amino acid substitution at a given sequence position affects a protein's function based on sequence homology. See Ferrer-Costa et al., (2005), Bioinformatics, 21(14):3176-3178; Ferrer-Costa et al., (2004), Proteins, 57(4):811-819; and Ferrer-Costa et al., (2002), J Mol Biol, 315:771-786. The SIFT algorithm server is publicly available on the world wide web at: blocks.fhcrc.org/sift/SIFT.html. Thus, for any IF functional homolog amino acid sequence, an "amino acid substitution matrix" can be generated that provides the predicted neutrality or deleteriousness of any given amino acid substitution on IF function.

In preferred embodiments, where an amino acid is to be substituted within one of the IF reference sequences disclosed herein, the amino acid substitution is a conservative amino acid substitution. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Non-naturally occurring sequence variants can be generated by a number of known methods. Such methods include, but are not limited to, "Gene Shuffling," as described in U.S. Pat. No. 6,521,453; "RNA mutagenesis," as described in Kopsidas et al., (2007), BMC Biotechnology, 7:18-29; and "error-prone PCR methods." Error prone PCR methods can be divided into (a) methods that reduce the fidelity of the polymerase by unbalancing nucleotides concentrations and/ or adding of chemical compounds such as manganese chloride (see, e.g., Lin-Goerke et al., (1997), *Biotechniques*, 23:409-412), (b) methods that employ nucleotide analogs (see, e.g., U.S. Pat. No. 6,153,745), (c) methods that utilize 'mutagenic' polymerases (see, e.g., Cline, J. and Hogrefe, H. H. (2000), *Strategies* (Stratagene Newsletter), 13:157-161 and (d) combined methods (see, e.g., Xu et al., (1999), *Biotechniques*, 27:1102-1108. Other PCR-based mutagenesis methods include those, e.g., described by Osuna et al., (2004), *Nucleic Acids Res.*, 32(17):e136 and Wong et al., (2004), *Nucleic Acids Res.*, 10; 32(3):e26), and others known in the art.

In some embodiments, forced expression of IFs factors in hPSCs is achieved by any of a number of established methods to introduce a mammalian expression vector, e.g., viral transduction, lipofection, electroporation, or nucleofection. In some embodiments mammalian expression vectors to be used are double-stranded nucleic acid vectors (e.g., episomal plasmid vectors, transposon vectors, or minicircle vectors). Mammalian expression vectors suitable for the methods described herein comprise a promoter competent to drive IF expression in hPSCs. Examples of suitable promoters for driving IF expression in hPSCs include, but are not limited to, constitutive promoters such as, EF-1-α, CAG, Ubiquitin (UbC), cytomegalovirus (CMV), HSV1-TK, SV40, β-actin; PGK, and inducible promoters, such as those containing TET-operator elements.

In some embodiments, a mammalian expression vector used herein comprises a polycistronic expression cassette, i.e., an expression cassette that encodes a "polyprotein" comprising multiple polypeptide sequences that are separated by encoded by a picornavirus, e.g., a foot-and-mouth disease virus (FMDV) viral 2A peptide sequence. The 2A peptide sequence acts co-translationally, by preventing the formation of a normal peptide bond between the conserved glycine and last proline, resulting in ribosome skipping to the next codon, and the nascent peptide cleaving between the Gly and Pro. After cleavage, the short 2A peptide remains fused to the C-terminus of the 'upstream' protein, while the proline is added to the N-terminus of the 'downstream' protein, which during translation allow cleavage of the nascent polypeptide sequence into separate polypeptides. See, e.g., Trichas et al (2008), BMC Biol, 6:40.

In other embodiments, a polycistronic expression cassette may incorporate one or more internal ribosomal entry site (IRES) sequences between open reading frames incorporated into the polycistronic expression cassette. IRES sequences and their use are known in the art as exemplified in, e.g., Martinez-Salas (1999), *Curr Opin Biotechnol*, 10(5):458-464.

In some embodiments forced expression of an IF is carried out by transducing hPSCs with one or more recombinant expression viruses carrying DNA or RNA encoding one or more of the above-described IFs. Examples of recombinant viruses include, but are not limited to, retroviruses (including lentiviruses); adenoviruses; adeno-associated viruses, Herpes Simplex virus (HSV), and RNA viruses such as Sendai (RNA) virus.

In one embodiment, forced expression of IFs in hPSCs is carried out by use of recombinant lentiviruses comprising an EF-α promoter to drive expression of bicistronic expression cassettes encoding an IF and linked by way of an IRES sequence to a selection marker, e.g., a protein encoding resistance to puromycin. Typically, where lentiviruses are used, hPSCs are transduced in single cell suspension in complete TeSR1™ medium at a concentration of about $0.5 \times 10^6$ to $1 \times 10^6$ $6.8 \times 10^5$ cells/ml in the presence of a Rho kinase inhibitor, e.g., Y27632 (10 µg/ml) and polybrene (6 µg/ml) at a multiplicity of infection (MOI) of about 1 to 5. The hPSC and virus-containing medium suspension is then plated on Matrigel™-cell culture plates and incubated for about 12 hours, after which the medium is replaced with fresh TeSR1™ medium, and the cells incubated for another 12 hours prior to culturing in growth-factor supplemented medium as described above.

In some embodiments double stranded DNA expression vectors ("DNA expression vectors") are used to express IFs as described herein. In some embodiments, the DNA expression vectors used in the reprogramming methods described herein also include loxP transposition target sites for CRE recombinase, which allows for subsequent excision of the vector. In other embodiments DNA expression vectors are episomal vectors that are stably maintained and replicate within host mammalian cells without genomic integration. Episomal vectors include a mammalian origin of replication, e.g., the Epstein-Barr Virus oriP element (Yates et al (1984), Proc. Natl. Acad. Sci. USA, 81:3806-3810, which allows episomal replication of the DNA expression vector in the hPSCs. Examples of vectors comprising a mammalian origin of replication are described in, e.g., U.S. Pat. No. 8,546,140. Episomal DNA expression vectors suitable for the methods described herein include, but are not limited to, any of the following episomal vectors: pCEP4, pREP4, or pEBNA DEST. In some embodiments, the DNA expression vectors suitable for the methods described herein include a S/MAR (scaffold/matrix attachment region) sequence. See, e.g., Piechaczek et al (1999), Nucleic Acids Res, 27:426-428.

In some embodiments, the mammalian expression vectors to be used are piggyBac transposon expression vectors, which are efficiently integrated into the genome of mammalian cells when transfected into the mammalian cells in the presence of a piggyBac transposase. Subsequently, a piggyback transposon can be excised from the genome of recombinant host cells, by transiently expressing a piggyback transposase. See, e.g., Yusa et al (2011), *Proc. Natl Acad. Sci USA*, 108:1531-1536.

In some embodiments forced expression of IFs is achieved by introduction of modified mRNAs (mmRNAs) encoding IFs into hPSCs, e.g., by electroporation. mmRNAs and their synthesis is described in detail in, e.g., U.S. Patent Application Publication No 20120046346. Typically, mmRNAs comprise (i) a 5' synthetic cap for enhanced translation; (ii) modified nucleotides that confer RNAse resistance and an attenuated cellular interferon response, which would otherwise greatly reduce translational efficiency; and (iii) a 3' poly-A tail. Typically, IF mmRNAs are synthesized in vitro from a DNA template comprising an SP6 or T7 RNA polymerase promoter-operably linked to an open reading frame encoding an IF. The mmRNA synthesis reaction is carried in the presence of a mixture of modified and unmodified nucleotides. In some embodiments modified nucleotides included in the in vitro synthesis of mmRNAs are pseudouridine and 5-methyl-cytosine. A key step in cellular mRNA processing is the addition of a 5' cap structure, which is a 5'-5' triphosphate linkage between the 5' end of the RNA and a guanosine nucleotide. The cap is methylated enzymatically at the N-7 position of the guanosine to form mature mCAP. When preparing IF mmRNAs, a 5' cap is typically added prior to transfection of hPSCs in order to stabilize IF mmRNA and significantly enhance translation. In some embodiments a 4:1 mixture of a cap analog to GTP is used in transcription reactions to obtained 5'-capped mmRNAs. In preferred embodiments, the Anti Reverse Cap Analog (ARCA), 3'-O-Me-m7G(5')ppp(5')G is used to generate IF mmRNAs that can be efficiently translated in hPSCs. Systems for in vitro synthesis are commercially available, as exemplified by the mRNAExpress™ mRNA Synthesis Kit (System Biosciences, Mountain View, Calif.).

IF mmRNAs can be introduced into hPSCs by any of a number of established methods for transfection of mammalian cells, e.g., electroporation, nucleoporation, or lipofection. In one exemplary embodiment IF mmRNAs are introduced into hPSCs by nucleoporation as follows.

Nucleofection of IF mRNAs into hPSCs is performed using an Amaxa Human Stem Cell Nucleofector® Kit 2. Prior to nucleofection, cells are washed with PBS and dissociated to a single cell suspension using Accutase® (Invitrogen) and collected in TeSR1™ medium containing 10 µg/ml ROCK inhibitor (Y27632). For one/well reaction $1.5 \times 10^6 - 2 \times 10^6$ cells are resuspended in 100 µl of nucleofection reagent containing mmRNA (1.75 µg of both GATA2 and ETV2; 3.5 µg in total), transferred immediately to nucleofection cuvette, and nucleofected using the B-016 program on the Amaxa Nucleofector II. After the procedure, cells are resuspended in 500 µl of TeSR1™ medium with ROCK Inhibitor (Y27632) and transferred to Matrigel™ coated six-well plates containing two ml of TeSR1™ media. Cells are then cultured in a regular TeSR1™ medium for the first 24 hours followed by a change to growth factor-free TeSR1™ base medium containing SCF (100 ng/ml), TPO (50 ng/ml) and bFGF (20 ng/ml).

In other embodiments, IF proteins s are generated by in vitro translation and then transduced into hPSCs. In some cases, protein transduction method includes contacting cells with a composition containing a carrier agent and at least one purified polypeptide comprising the amino acid sequence of one of the above-mentioned IFs. Examples of suitable carrier agents and methods for their use include, but are not limited to, commercially available reagents such as Chariot™. (Active Motif, Inc., Carlsbad, Calif.) described in U.S. Pat. No. 6,841,535; Bioport®. (Gene Therapy Systems, Inc., San Diego, Calif.), GenomeONE (Cosmo Bio Co., Ltd., Tokyo, Japan), and ProteoJuice™. (Novagen, Madison, Wis.), or nanoparticle protein transduction reagents as described in, e.g., in U.S. Pat. No. 7,964,196.

The protein transduction method may comprise contacting hPSCs with at least one purified polypeptide comprising the amino acid sequence of one of the above-mentioned TAs fused to a protein transduction domain (PTD) sequence (IF-PTD fusion polypeptide). The PTD domain may be fused to the amino terminal of an IF sequence; or, the PTD domain may be fused to the carboxy terminal of an IF sequence. In some cases, the IF-PTD fusion polypeptide is added to cells as a denatured polypeptide, which may facilitate its transport into cells where it is then renatured.

Generation of PTD fusion proteins and methods for their use are established in the art as described in, e.g., U.S. Pat. Nos. 5,674,980, 5,652,122, and 6,881,825. See also, Becker-Hapak et al (2003), Curr Protocols in Cell Biol, John Wiley & Sons, Inc. Exemplary PTD domain amino acid sequences include, but are not limited to, any of the following:

```
                                        (SEQ ID NO: 8)
YGRKKRRQRRR;;

(SEQ ID NO: 9)
RKKRRQRR (SEQ ID NO: 10)
YARAAARQARA;

(SEQ ID NO: 11)
THRLPRRRRRR;
and (SEQ ID NO: 12)
GGRRARRRRRR.
```

III. Compositions

Also described herein are compositions useful for carrying out the hPSC differentiation methods described above.

In some embodiments disclosed herein are recombinant human pluripotent stem cells (hPSCs) that comprise: (i) one or more exogenous nucleic acids suitable for expression of any of the combinations of IFs listed in Table 1 or Table 2, or functional homologs thereof; (ii) exogenous polypeptides each of which comprises the amino acid sequence of an IF or a functional homolog thereof.

In some embodiments the recombinant human pluripotent stem cells are integration-free. In some embodiments, where the recombinant hPSCs are integration-free, the hPSCs contain one or more episomal mammalian expression vectors, recombinant viral RNAs (e.g., a Sendai virus RNA genomes), or mmRNAs encoding any of the IF combinations described in Table 1 or Table 2. In other embodiments the recombinant human PSCs comprise exogenous polypeptides comprising the amino acid sequence of any of the IFs for the combinations listed in Table 1 or Table 2, or functional homologs thereof. In some embodiments the recombinant hPSCs are recombinant hiPSCs. In other embodiments the recombinant hPSCs are recombinant hESCs In some embodiments, recombinant hPSCs are provided as a cell culture composition for generating hemogenic endothelial cells with pan myeloid potential, where the cell culture composition comprises recombinant hPSCs and a cell culture medium suitable for expansion of hematopoietic cells. In some embodiments, a suitable cell culture medium includes FGF2, SCF, and TPO.

Also disclosed herein is a kit for hemogenic reprogramming, comprising:

(i) one or more isolated nucleic acids comprising an open reading frame for (a) ETV2 or ERG, and GATA1; (b) ETV2 or ERG, and GATA2; (c) ETV2 or ERG, and GFI1; or (c) TAL1 and GATA2; or (ii) one or more recombinant expression viruses (e.g., retroviruses or lentiviruses) suitable for expression, in human pluripotent stem cells, of (a) ETV2 or ERG, and GATA1; (b) ETV2 or ERG, and GATA2; (c) ETV2 or ERG, and GFI1; or (c) TAL1 and GATA2.

In some embodiments, the one or more isolated nucleic acids provided in the kit are DNA expression vectors. In other embodiments, the provided nucleic acids are modified mRNAs.

EXAMPLES

Example 1 A Screen for Hematopoietic Induction Factors

Human pluripotent stem cells (hPSCs), including embryonic stem cells (hESCs) and induced PSCs (hiPSCs) offer a plentiful source of blood cells for experimentation and therapeutic purposes. Although significant advances have been made in hematopoietic differentiation from hPSCs, a better understanding of key regulators of hematopoietic commitment is required to achieve the scalability of blood cells production from hPSCs and enable de novo generation of hematopoietic stem cells (HSCs).

Transcription factors (TFs) have been recognized as critical regulators of early embryonic development. They function as key elements of gene regulatory network that guide the acquisition of specific properties defining each particular cell type (1). Several TFs have been identified as master regulators of hematopoietic development in mouse embryo (2-5). Many of them are also involved in the regulation of endothelial development reflecting a close developmental link between endothelial and hematopoietic cells (6). In fact, recent studies have demonstrated that in the embryo, hematopoietic cells, including HSCs, arise from endothelial cells with blood-forming potential, hemogenic endothelium (HE) (7-9), indicating that blood development proceeds through an endothelial intermediate stage. To unravel the most essential TFs required for the induction of the blood program from hPSCs, we performed comprehensive gain-of-function screens. Using this approach we identified two groups of TFs capable of inducing the distinct robust hematopoietic programs from PSCs: pan-myeloid (ETV2 and GATA2) and erythro-megakaryocytic (TAL1 and GATA2). Interestingly, both TF combinations directly induced hemogenic endothelial (HE) cells, which subsequently transformed into blood cells. These results strongly indicate that specification to discrete types of hematopoietic progenitors begins at the HE stage and is regulated by distinct transcriptional programs. In addition, we also demonstrated the ability of modified mRNA (mmRNA) encoding TFs to induce a hematopoietic program in hPSCs without the risk of genomic modifications.

Materials and Methods
Cloning of Selected Genes and Virus Production

Open Reading Frames (ORFs) of selected genes were amplified from cDNA of H1 hESCs differentiated in co-culture with OP9, or from full-length cDNAs clones obtained from Open BioSystems and Gene Copoeia Inc. After sequence verification, ORFs were subcloned into pSIN/EF1α-IRES-Puro lentiviral expression vector. Virus production was carried out by calcium phosphate transfection of 293T cells. Packaged lentiviral units were concentrated on gas-sterilized Centricon Plus-70 or Amicon Ultra-15 Centrifugal Filter Units (Millipore) or by ultracentrifugation at 33,000 rpm for 2.5 hr and re-suspended in 1% BSA in PBS. Lentiviral stocks were titrated using puromycin resistant HeLa cells (working concentration of puromycin 1 µg/ml), and stored at −80 C.

Cell Culture and hPSC Transduction hESC lines H1 (WA01), H9 (WA09) and fibroblast-derived hiPSC (DF-19-9-7T and DF-4-3-7T) were obtained from WiCell Institute Madison, Wis. Cell were maintained and expanded in undifferentiated states on mouse embryonic fibroblasts. Prior to lentiviral transduction, hESCs were transferred on Matrigel™ and grown in feeder free conditions from two to five passages. After treatment with Accutase® (Invitrogen), hESCs were transduced in a single cell suspension at concentration $0.68 \times 10^6$ cells/ml, in the presence of ROCK Inhibitor (10 µg/ml, Stemgent), Polybrene (6 µg/ml, Sigma) and virus (MOI=1-5). Treated cells were plated on 6 well Matrigel™ coated plates (1 ml/well), and incubated for 12 hours. Viral medium was replaced with fresh TeSR1™ and incubated for another 12 hours. On day 1 after transduction, regular TeSR1™ was replaced with TeSR1-growth-factor-free, supplemented with SCF (100 ng/ml), TPO (50 ng/ml) and FGF2 (20 ng/ml). Cells were maintained in indicated conditions from three to seven days, depending on their survival and growth, and collected for analysis.

Nucleofection of Human Pluripotent Stem Cells with Modified mRNAs

Nucleofection of H1 hESCs with modified messenger RNAs (mmRNAs) was performed using Amaxa Human Stem Cell Nucleofector® Kit 2. Prior to nucleofection, cells were washed with PBS and dissociated to a single cell suspension using Accutase® (Invitrogen) and collected in TeSR1™ medium containing 10 µg/ml Rock inhibitor. For one/well reaction $2 \times 10^6$ cells were resuspended in 100 µl nucleofection reagent containing mmRNA (1.75 µg of both GATA2 and ETV2; 3.5 µg in total), transferred immediately to nucleofection cuvette and nucleofected using the B-016 program on the Amaxa Nucleofector II. After the procedure, cells were resuspended in 500 µl of TeSR1™ medium with Rock Inhibitor and transfer to Matrigel™ coated 6-well plates containing 2 ml of TeSR1™ media. Cells were kept in a regular TeSR1™ medium for the first 24 hours followed by the change to differentiation medium containing SCF (100 ng/ml), TPO (50 ng/ml) and bFGF (20 ng/ml).

Immunostaining Procedures

Expression of cell-surface proteins was assessed by routine flow cytometry protocol (FACSCalibur, BD Biosciences). For intracellular staining by FACS, cells were fixed for 10 minutes at 37° C. in Cytofix buffer (BD Biosciences), followed by permeabilization for 30 minutes on ice in Perm Buffer III (BD Biosciences). After washing, cells were stained at 40° C. for 2 hours with fluorescence-conjugated antibodies. For detection of protein expression and cellular localization by immunofluorescence, cells were fixed with 4% paraformaldehyde on culture plates, permeabilized with 0.01% of Triton X-100, and stained overnight at 40° C. with primary antibodies, followed by staining with the secondary fluorochrome-labeled antibodies. Intranuclear staining of pluripotency markers was performed by permeabilization with ice-cold 0.2% Triton X-100 in PBS. All antibodies used in this study are listed in Table 4.

Hematopoietic Colony-Forming Assay

Hematopoietic clonogenic assays were performed using serum-containing methylcellulose medium (MethoCult) supplemented with SCF, G-CSF, GM-CSF, IL3, IL6, and EPO (Stem Cell Technologies) according to the manufacture's protocol. Wright staining was used to evaluate the morphology of cells within colonies.

Endothelial Assays

Endothelial differentiation was assessed as previously described. (10) On day 7 post-transduction, TF-induced cells were placed on fibronectin-coated 6-well plates (hFibronectin, BD) supplemented with complete Endothelial Cell Medium ECM (ScienCell). For AcLDL uptake assay, cells growing in monolayer were incubated with 10 μm/ml of Alexa-594- or Alexa-488-conjugated AcLDL (Invitrogen, cat. #L-35353 and L-23380 correspondingly) for four hours at 37° C. followed by fluorescent microscopy or flow cytometry analysis. For vascular tube formation, $2 \times 10^4$ cells were resuspended in ECM medium supplemented with VEGF 40 ng/ml and plated on a solidified Matrigel™-coated 96-well plate. Cells were incubated at 37° C., 5% $CO_2$ for 18-24 hours when tube formation was observed.

Evaluation of Hemogenic Potential of Transduced Cells at Endothelial Stage

Cells transduced with recombinant viruses for TF expression were collected at day 3 post-transduction and labeled with VE-cadherin, CD43, and CD73 antibodies. Individual VE-cadherin$^+$CD43$^-$CD73$^-$ cells were then deposited into 96-well plates on an OP9 monolayer using FACSAria™ cell sorter, cultured for two weeks and analyzed for CD43 and VE-cadherin expression by immunostaining.

Quantitative RT-PCR/PCR

RNA isolation was carried out with RNeasy Micro Kit (Qiagen). RNA concentration and quality was evaluated by nano-drop followed by cDNA synthesis using AdvantageRT-for-PCR Kit (Clontech). qPCR was performed using SYBR® Advantage® qPCR Premix (Clontech). Genomic DNA was isolated using NucleoSpin Tissue XS kit (Macherey-Nagel), and PCR was carried out with Tag 2× MasterMix (New England BioLabs Inc).

RNA-Seq Analysis

Total RNA was isolated using RNeasy Micro Kit (Qiagen, cat #74004). Treatment with DNaseI was performed on the column according to the manufacture's protocol. Purity and integrity of RNA was estimated by the capillary electrophoresis on the Bioanalyzer 2100 (Agilent Technologies). PolyA+ RNAs were amplified using a modified T7 amplification method as previously described (Sengupta at al., 2010). cDNA samples were quantified with the Qubit Fluorometer (Invitrogen) and sequenced on the Illumina Genome Analyzer IIx.

Time-Lapse Microscopy

To capture the endothelial-hematopoietic transition, the time-lapse movies were recorded using Nikon Eclipse Ti-E configured with an A1R confocal system and motorized stage (Nikon Instruments Inc. Melville, N.Y.). Cell culture surfaces were washed thoroughly to remove debris, and VE-cadherin-FITC and CD43-PE antibodies were added to a final concentration of 100 ng/ml. Movies were made on day 2.5 post-transduction for GATA2/TAL1/LMO2-induced cells and on day 4 for GATA2/ETV2-induced cells. Images were acquired using Nikon Elements (NIS-element C) imaging software for every 5 minutes with CFI Plan Fluor DLL 20× NA 05 WD 2.1 MM objective (Nikon Instruments Inc. Melville, N.Y.). To convert time-lapse serial images to movies, the Quick-time movies and ImageJ (NIMH, Bethesda, Md.) software were applied.

Results

Selection of Candidate Genes and Screening System Design

Figure 6:
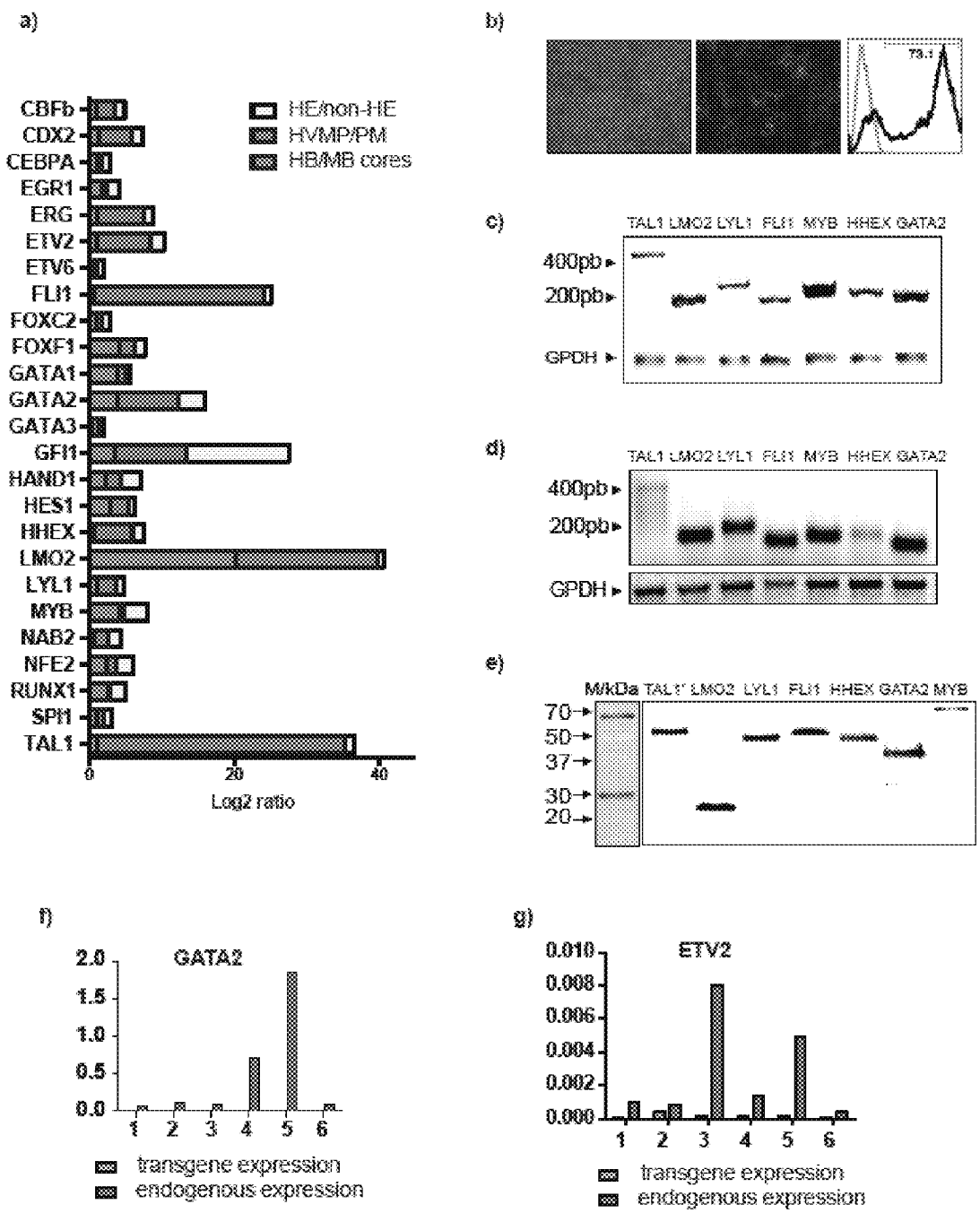
FIG. 6 Design of screening system. (a) TFs enriched in hESC-derived mesodermal and endothelial cells with hematopoietic activity (Maxim Vodyanik et al., 2010; Kung-Dal Choi et al., 2012). Bars represent a ratio of TF expression in indicated subpopulations obtained from hESCs differentiated in coculture with OP9 and analyzed by RNAseq. HE is VE-cadherin$^+$CD43$^-$CD73$^-$ hemogenic endothelium, non-HE (VE-cadherin$^+$CD43$^-$CD73$^+$) non-hemogenic endothelium, PM is apelin receptor positive primitive mesodermal cells with hemangioblast potential generated on day 3 hESC/OP9 coculture, HVMP is hematovascular mesodermal precursor highly enriched in cells forming hematoendothelial clusters on OP9 isolated on day 4 of differentiation, HB is endothelial intermediates (cores) with hematopoietic activity formed in hemangioblast clonogenic cultures, MB is endothelial intermediates (cores) without hematopoietic activity formed in mesenchymoangioblast clonogenic cultures. (b) Phase-contrast and fluorescent microscopy of H1 hESC transduced with eGFP-expressing virus, day 5 post-transduction (0.68×10$^6$ cells, MOI=0.5). Right panel shows efficiency of lenti-viral transduction in hESCs by FACS analysis. (c) PCR analysis of virus integration into genome. 10$^4$ H1 cells transduced with indicated constructs were collected for DNA isolation, followed by pSIN-EFa specific PCR. (d) RT-PCR of indicated transgenes in HeLa cells transduced with indicated constructs. (e) Western blot analysis shows overexpressed proteins in HeLa cells transduced with corresponding pSIN-EF1a expression vectors: SCL-FLAG, LMO2-FLAG, LYL1-FLAG, HHEX-HA, GATA2-HA, FLI1-myc, MYB-myc; (f, g) Real-time PCR analysis of transgene and endogenous expression of ETV2 and GATA2 transcripts in hematopoietic colonies derived from ETV2 and GATA2 transduced cells on day 21 post-transduction.

To induce the hematopoietic program in hPSCs, we first assembled a list of candidate transcriptional regulators involved in mesodermal and angiohematopoietic specification and HSC development through a literature review. To prioritize the list of genes for screening, we used molecular profiling data obtained from the analysis of gene expression of hESC-derived mesodermal and vascular progenitors with and without hematopoietic potential (10,11). Based on this data we selected 27 genes (Table 3 and FIG. 6a).

TABLE 3

List of Candidate Transcription Factors ("Induction Factors")

| | TRANSCRIPTION FACTOR | SEQUENCE (human) |
|---|---|---|
| 1 | CBFB<br>Core-binding factor subunit beta (CBF-beta) | NM_001755.2 |
| 2 | CDX2<br>Caudal type homeobox 2 | NM_001265.4 |
| 3 | CEBAa<br>CCAAT/enhancer binding protein (C/EBP), alpha | BC160133.1 |
| 4 | EGR1<br>Early growth response 1 | NM_001964.2 |
| 5 | ERG<br>v-ets erythroblastosis virus E26 oncogene homolog (avian) ETS-related gene; transcriptional regulator ERG | NM_001243428.1<br>(SEQ ID NO: 3) |
| 6 | ETV2<br>ETS translocation variant 2 | NM_014209.2<br>(SEQ ID NO: 1) |
| 7 | ETV6<br>ets variant 6 | NM_001987.4 |
| 8 | FOXF1<br>Forkhead box F1 | NM_001451.2 |
| 9 | FOXC2<br>Forkhead box C2 (MFH-1, mesenchyme forkhead 1) | BC113439.1 |
| 10 | FLI1<br>Friend leukemia virus integration 1 | NM_002017.3 |
| 11 | GATA1<br>GATA binding protein 1, globin transcription factor 1 | NM_002049.3<br>(SEQ ID NO: 2) |
| 12 | GATA2<br>GATA binding protein 2, endothelial transcription factor GATA-2 | BC051342.1<br>(SEQ ID NO: 4) |
| 13 | GATA3<br>GATA binding protein 3 trans-acting, T-cell-specific transcription factor GATA-3 | BC003070.2 |
| 14 | GFI1<br>Growth factor independent 1 transcription repressor | BC032751.1<br>(SEQ ID NO: 5) |
| 15 | HAND1<br>Heart and neural crest derivatives expressed 1 | NM_004821.2 |
| 16 | HES1<br>Hairy and enhancer of split 1, (Drosophila) | NM_005524.3 |
| 17 | HHEX<br>Hematopoietically expressed homeobox | NM_002729.4 |
| 18 | LMO2<br>LIM domain only 2 (rhombotin-like 1) | NM 001142315.1<br>(SEQ ID NO: 7) |
| 19 | LYL1<br>Lymphoblastic leukemia derived sequence 1 | NM_005583.4 |
| 20 | MYB<br>v-myb myeloblastosis viral oncogene homolog (avian) | BC064955.1 |
| 21 | NAB2<br>NGFI-A binding protein 2 (EGR1 binding protein 2) | BC065931.1 |
| 22 | NFE2<br>Nuclear factor (erythroid-derived 2), 45 kDa | BC005044.1 |
| 23 | RUNX1 isoform RUNX1A<br>Runt-related transcription factor 1 (RUNX1) transcript variant 3 Acute myeloid leukemia 1 protein isoform a | NM_001122607.1 |
| 24 | RUNX1 isoform RUNX1B<br>Runt-related transcription factor 1 (RUNX1) transcript variant 2 Acute myeloid leukemia 1 protein isoform b | NM_001001890.2 |
| 25 | RUNX1 isoform RUNX1C<br>Runt-related transcription factor 1 (RUNX1) transcript variant 1 Acute myeloid leukemia 1 protein isoform c | NM_001754.4 |

TABLE 3-continued

List of Candidate Transcription Factors ("Induction Factors")

| | TRANSCRIPTION FACTOR | SEQUENCE (human) |
|---|---|---|
| 26 | SPI1<br>Spleen focus forming virus (SFFV) proviral integration oncogene spi1, PU-box binding protein (PU.1) | NM_003120.2 |
| 27 | TAL1/SCL<br>T-cell acute lymphocytic leukemia 1 | NM_003189.2<br>(SEQ ID NO: 6) | file, while, in the case of some of the candidate genes, transduced hESCs yielded a differentiated phenotype, as described below.

Figure 7:
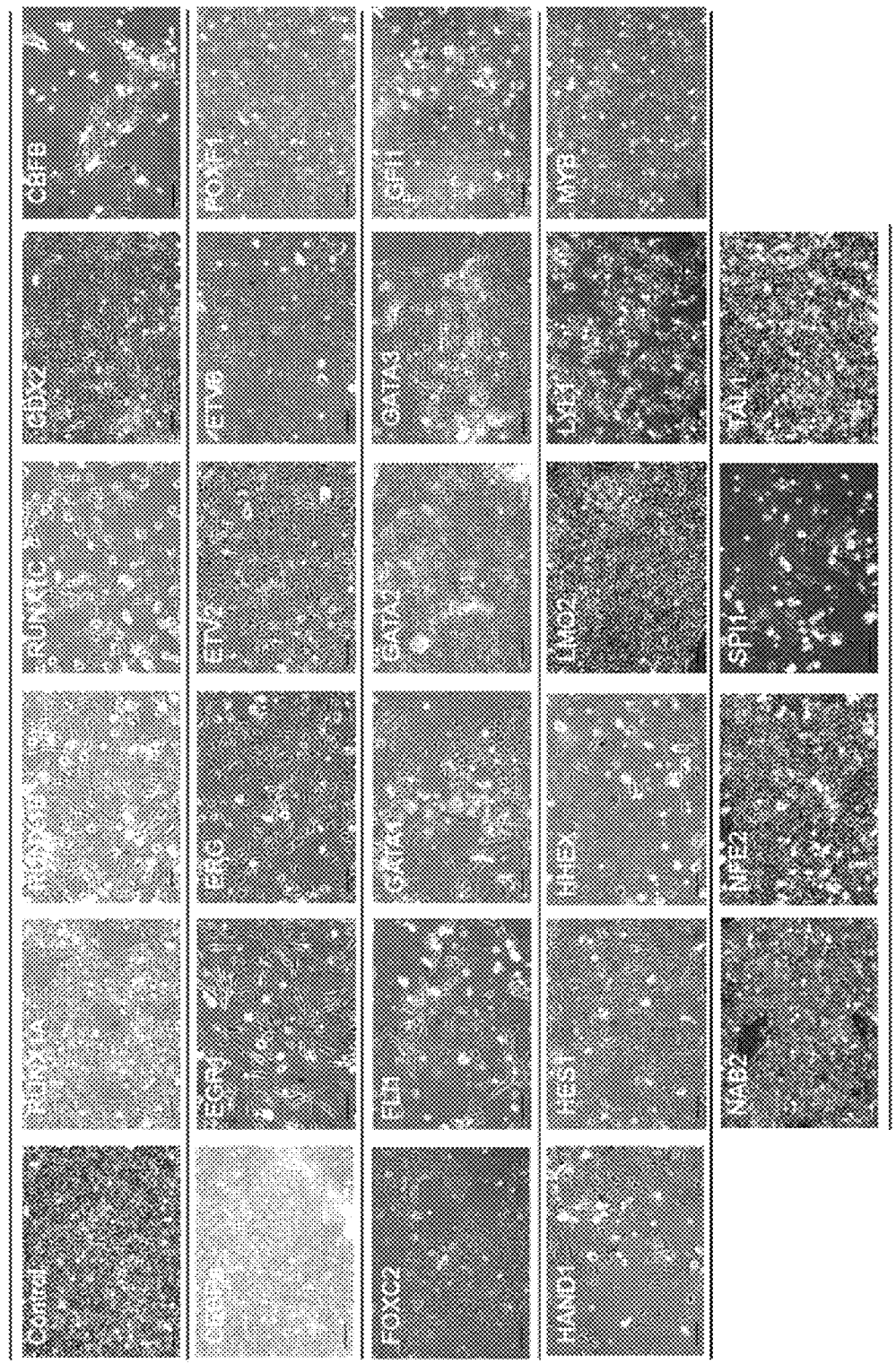
FIG. 7 Morphologies of hESCs differentiated by the overexpression of single transcription factors. Phase-contrast microscopy of H1 hESCs cultures transduced with indicated transcription factors. Photographs were taken at the day of cell collection as indicated in Table 4. Scale bar, 100 μm.

Single Factor Screening Identified ETV2 and ERG as TFs Sufficient for Direct Induction of Endothelium from hESCs To test the functional capacity of individual genes, we analyzed their effect on morphology, and expression of various mesodermal, endothelial, and hematopoietic markers by flow cytometry 7 days after transduction: APLNR and KDR (mesodermal), VE-cadherin, CD34 CD31 and CD73 (endothelial), and CD43 and CD45 (hematopoietic). Morphologic evaluation of cultures revealed three types of outcomes of TF overexpression: (1) a change in morphology, (2) no apparent change in morphology, and (3) cell death (Table 4 and FIG. 7).

TABLE 4

Differentiation Effects of Transcription Factors (Induction Factor Candidates)

| | Factor | Change morphology | Cell Death* | Day of Collection | Markers by FACS* | | | | | | | |
|---|---|---|---|---|---|---|---|---|---|---|---|---|
| | | | | | APLNR | KDR | VEC | CD31 | CD73 | CD34 | CD43 | CD45 |
| 1 | CBFB | No | No | d 5 | − | − | − | − | − | − | − | − |
| 2 | CDX2 | No | No | d 5 | − | − | − | − | − | − | − | − |
| 3 | CEBPA | No | No | d 5 | − | − | − | − | − | − | − | − |
| 4 | EGR1 | Yes | Yes | d 5 | − | − | − | − | − | − | − | − |
| 5 | ERG | Yes | No | d 5 | − | − | ++++ | ++++ | +++ | ++ | − | − |
| 6 | ETV2 | Yes | No | d 7 | + | ++++ | ++++ | ++++ | ++++ | ++++ | + | + |
| 7 | ETV6 | Yes | No | d 5 | − | − | − | − | − | − | − | − |
| 8 | FOXF1 | Yes | Yes | d 3 | − | − | − | − | ++ | + | − | − |
| 9 | FOXC2 | No | Yes | d 3 | − | − | − | − | − | − | − | − |
| 10 | FLI1 | Yes | No | d 3 | − | − | − | ++ | − | − | − | − |
| 11 | GATA1 | Yes | No | d 5 | + | + | − | − | + | ++ | + | − |
| 12 | GATA2 | Yes | No | d 7 | ++ | ++ | + | + | − | ++ | + | − |
| 13 | GATA3 | Yes | No | d 7 | + | + | − | − | − | ++ | − | − |
| 14 | GFI1 | Yes | No | d 5 | − | − | − | − | − | − | − | − |
| 15 | HAND1 | Yes | No | d 5 | − | − | + | + | ++ | − | − | − |
| 16 | HES1 | No | No | d 5 | − | − | − | − | − | − | − | − |
| 17 | HHEX | Yes | No | d 5 | − | − | − | − | − | − | − | − |
| 18 | LMO2 | No | No | d 5 | − | − | − | − | − | − | − | − |
| 19 | LYL1 | No | No | d 5 | − | − | − | − | − | − | − | − |
| 20 | MYB | No | No | d 5 | − | − | − | − | − | − | − | − |
| 21 | NAB2 | No | Yes | d 5 | − | − | − | − | − | − | − | − |
| 22 | NFE2 | No | No | d 5 | − | − | − | − | − | − | − | − |
| 23 | SPI.1 | Yes | Yes | d 3 | − | − | − | − | − | − | − | + |
| 24 | RUNX1A | No | Yes | d 3 | + | − | + | − | + | − | − | − |
| 25 | RUNX1B | Yes | Yes | d 3 | + | − | + | − | + | − | − | − |
| 26 | RUNX1C | Yes | Yes | d 3 | + | − | + | − | + | − | − | − |
| 27 | SCL/TAL1 | No | No | d 5 | − | − | − | − | − | − | − | − |

| Symbol | Expression Levels | Positive cells (%) |
|---|---|---|
| − | Negative | 0-1 |
| + | Low | 2-5 |
| ++ | Moderate | 5-20 |
| +++ | High | 20-50 |
| ++++ | Very high | >50 |

Figure 2:
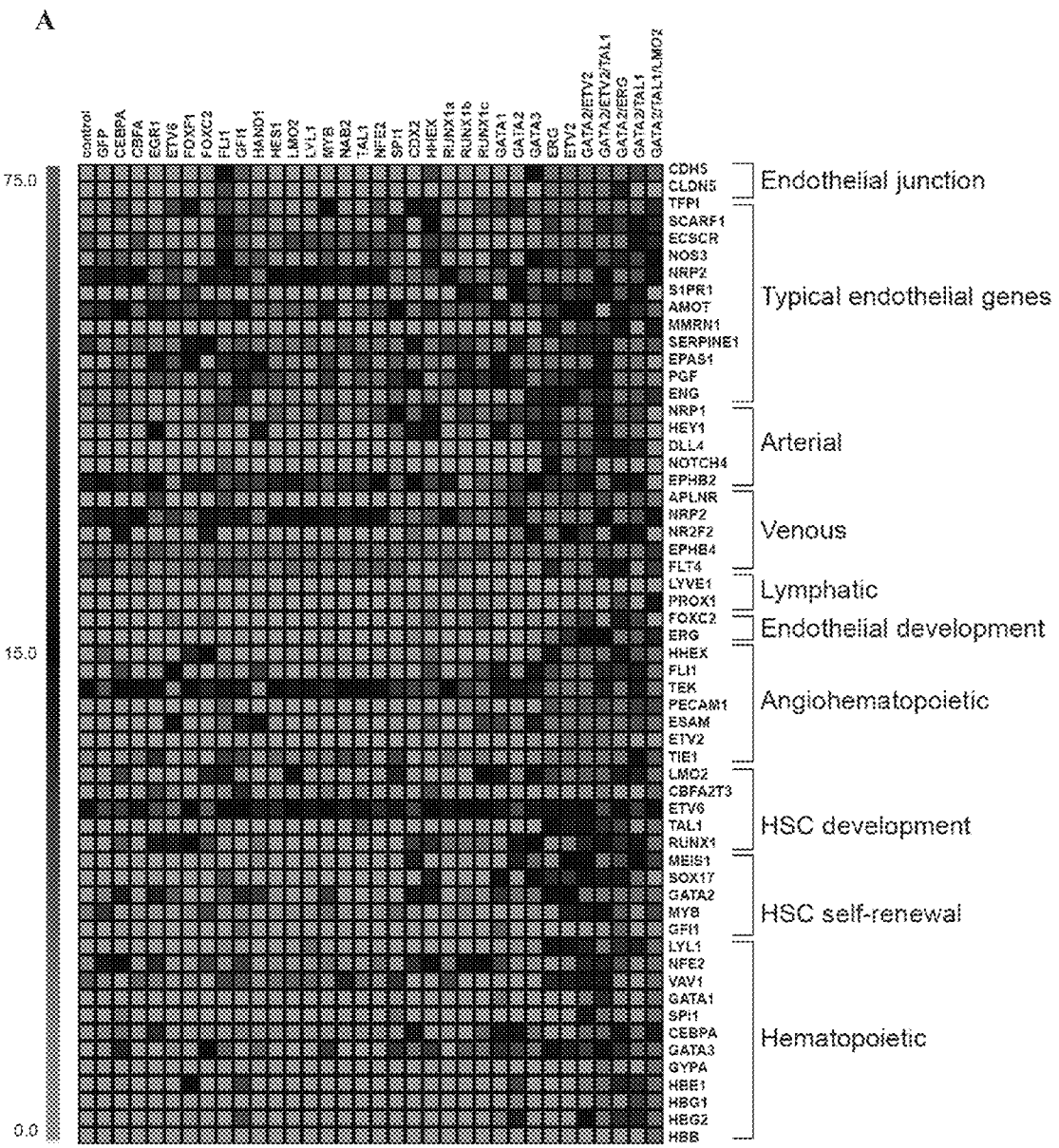
FIG. 2 Gene expression profiling of H1 hESCs differentiated by overexpression of single transcription factor and blood inducing combinations. (a) Heat map of selected sets of genes associated with endothelial and hematopoietic differentiation. (b) Heat map of selected set of genes associated with the development of germ layers and their derivatives.
Figure 2:
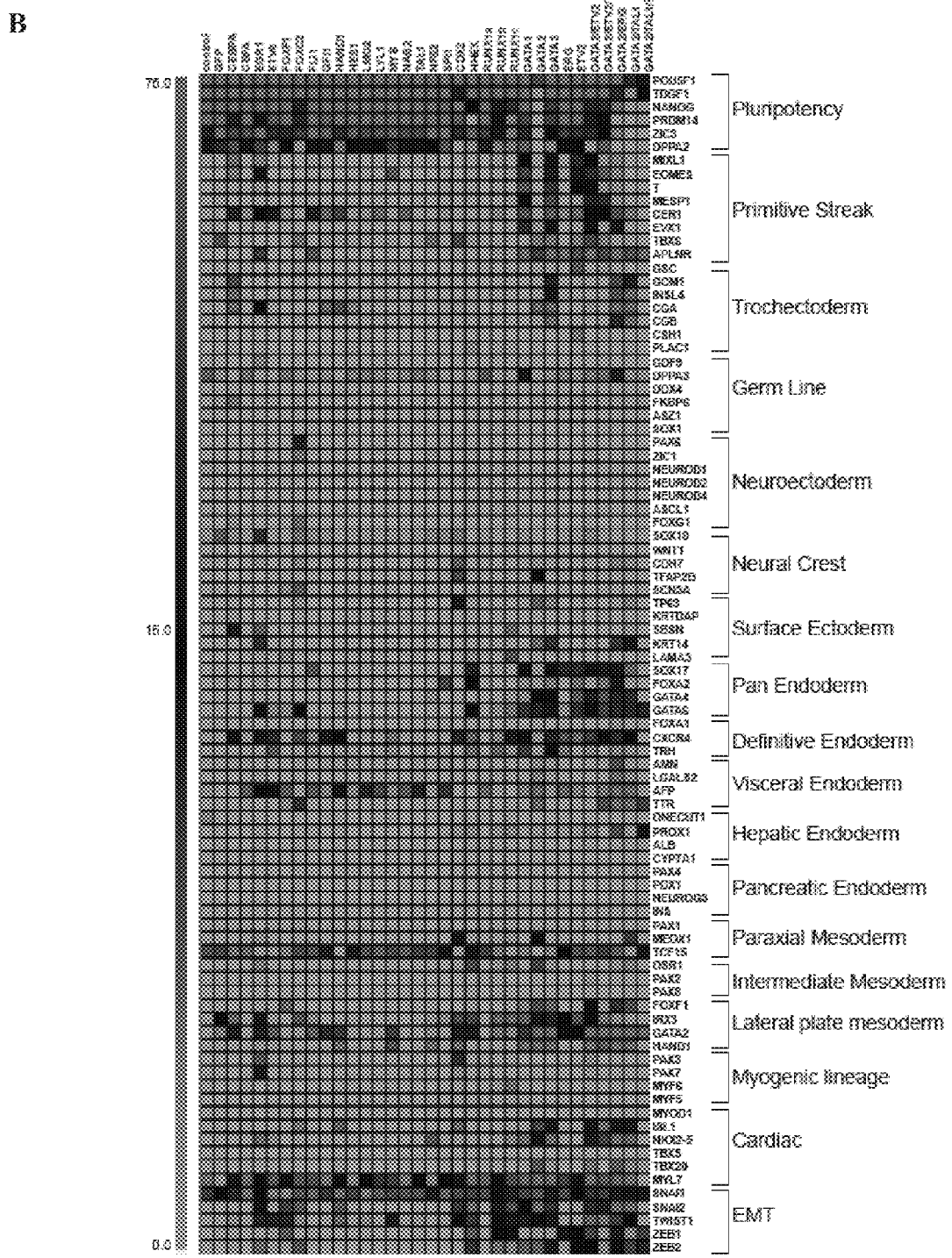

We assumed that the ideal hPSC-based system for a gain-of-function screen for hematopoiesis-inductive factors should meet two major requirements: (1) support the maintenance of untransduced hESCs or EGFP-transduced hPSCs in an undifferentiated state, (2) allow expansion of induced hematopoietic cells generated from hPSCs expressing a suitable combination of genes from our selected set of 27 genes. We found that these conditions were met by maintaining hPSCs as a monolayer on Matrigel™ in a serum-free TESR™1 medium supplemented with FGF2 and SCF and TPO hematopoietic cytokines. As shown in FIG. 1b-1e, in these conditions untransduced hESCs or EGFP-transduced hESCs remained visibly undifferentiated, retaining their morphology, cell surface markers and gene expression pro- Although in many cases morphologic changes were non-specific, we noticed that ETV2 and ERG induced the formation of cells with typical endothelial morphology. Immunofluorescent and functional analyses revealed that ETV2 and ERG-induced cells expressed VE-cadherin, CD31, CD34, TEK and KDR endothelial markers, showed AcLDL uptake, and formed vascular tubes in response to VEGF, consistent with endothelial nature of induced cells (FIG. 1e-1g). Gene expression analysis revealed that ETV2 or ERG alone are sufficient to induce expression of almost the entire set of genes required for angiohematopoietic development, and genes typically expressed in endothelial cells (FIG. 2a). However, they had little effect on expression of pluripotency genes. None of the selected genes were able to induce formation of round CD43$^+$ blood cells, though weak expression of CD43 by a very few epithelioid cells was noted following the transduction of cells with ETV2, GATA1 or GATA2 (Table 4). Although FOXF1 and HAND1 TFs are shown to be important for lateral plate/extraembryonic mesoderm development in mouse studies (12, 13), we found that they did not upregulate expression of APLNR or KDR pan-mesodermal markers or genes known to be expressed in lateral plate mesoderm. In contrast, we noticed that GATA2 overexpression by itself is a powerful activator of APLNR and KDR expression and repressor of ESC-specific genes (FIGS. 2a and 2b). Although GATA1 and GATA3 induced expression of many endothelial genes similar to GATA2, they also induced expression of primitive streak genes, but had little effect on expression of ESC-specific genes (FIG. 2b). Pearson correlation analysis of global gene expression revealed that ETV2, ERG, GATA1, GATA2, GATA3, HHEX, CEBPA, and EGR1 caused the most dramatic changes in gene expression, while LMO2, a transcriptional cofactor that which lacks DNA binding activity, and several DNA binding molecules, including, HES1, TAL1, LYL1 and CBFB, had minimal effect on gene expression in hESCs.

Figure 3:
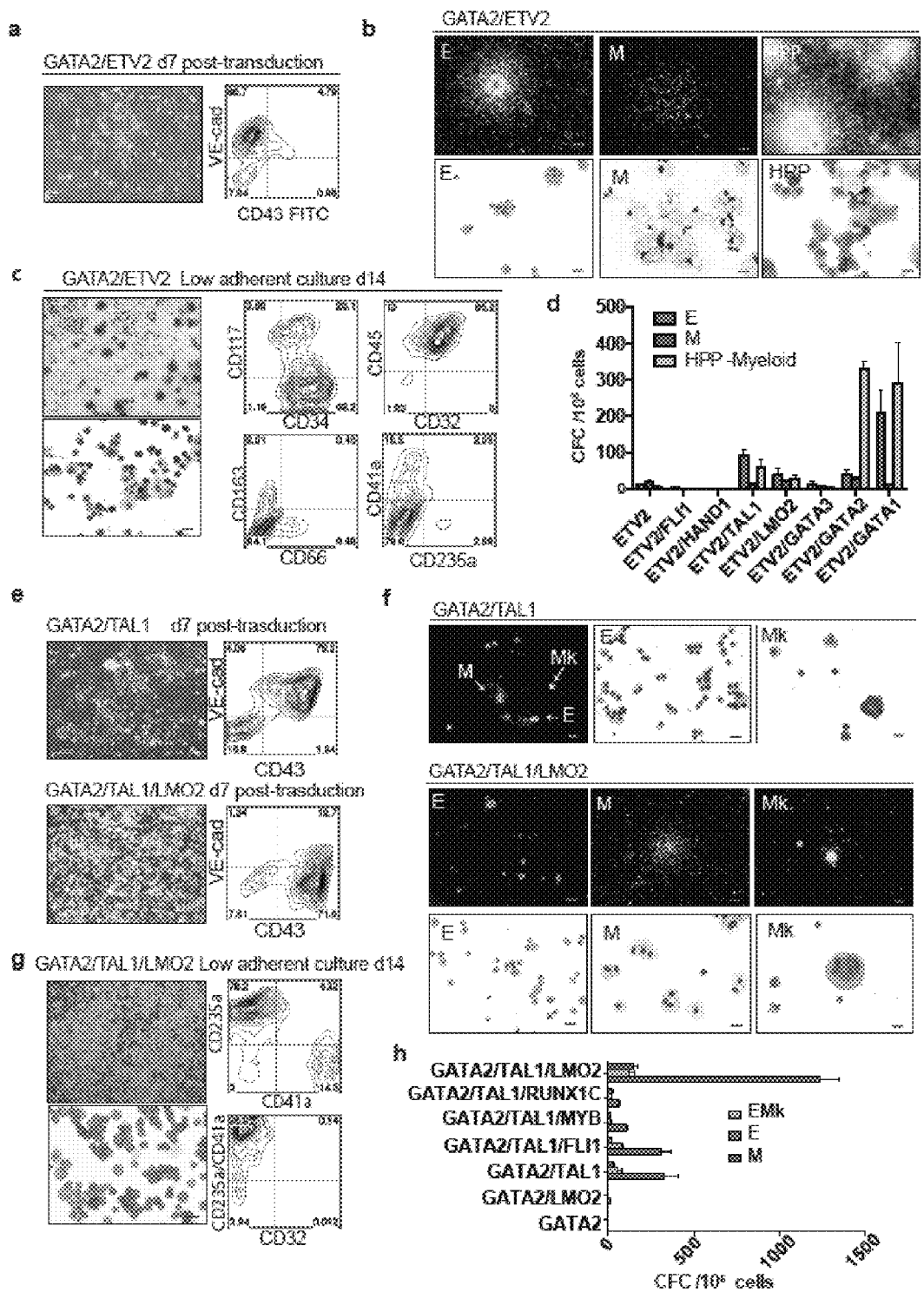
FIG. 3 Hematopoietic differentiation of hES cells induced by co-expression of GATA2/ETV2 and GATA2/TAL1 (LMO2). (a) Cell morphology and flow cytometric analysis of GATA2/ETV2-transduced H1 hESCs on day 7 post-transduction. Scale bar, 100 µm. (b) Types of hematopoietic colonies formed by GATA2/ETV2-transduced cells. Erythroid colonies (CFC-E); macrophage colonies (CFC-M); High Proliferative Potential (CFC-HPP) myeloid colonies containing predominantly myeloblasts with some granulocytes and macrophages. Scale bar for CFC-assay, 250 µm; cytospins, 20 µm. (c) Phase-contrast photograph of the culture, Wright-stained cytospin and FACS analysis of GATA2/ETV2-induced hematopoietic cells grown in low attachment culture for 14 days supplemented with 30% FBS and hematopoietic cytokines (SCF—100 ng/ml, IL3—10 ng/ml, IL6—20 ng/ml, GM-CSF—10 ng/ml, G-CSF—20 ng/ml, EPO—3 u/ml). (d) CFC potential of cells transduced with ETV2 and indicated TF combinations. Error bars represent SE from 2 to 5 independent experiments. (e) Cell morphology and flow cytometric analysis of H1 hESCs differentiated by expression of GATA2/TAL1 on day 7 post-transduction. (f) Types of hematopoietic colonies formed by GATA2/TAL1- and GATA2/TAL1/LMO2-differentiated cells. Erythroid colonies (CFU-E); macrophage colonies (CFU-M); Megakaryocytic colonies (CFU-Mk). Scale bar for CFC-assay, 250 µm; Scale bar on cytospins, 20 µm. (g) Phenotypic characterization of GATA2/TAL1/LMO2-induced hematopoietic cells grown in serum-free culture supplemented with SCF (100 ng/ml), TPO (50 ng/ml) and bFGF (20 ng/ml) for 14 days. (h) CFC potential of hESCs transduced with GATA2-based combinations. Error bars represent SE from 3 independent experiments.
Figure 8:
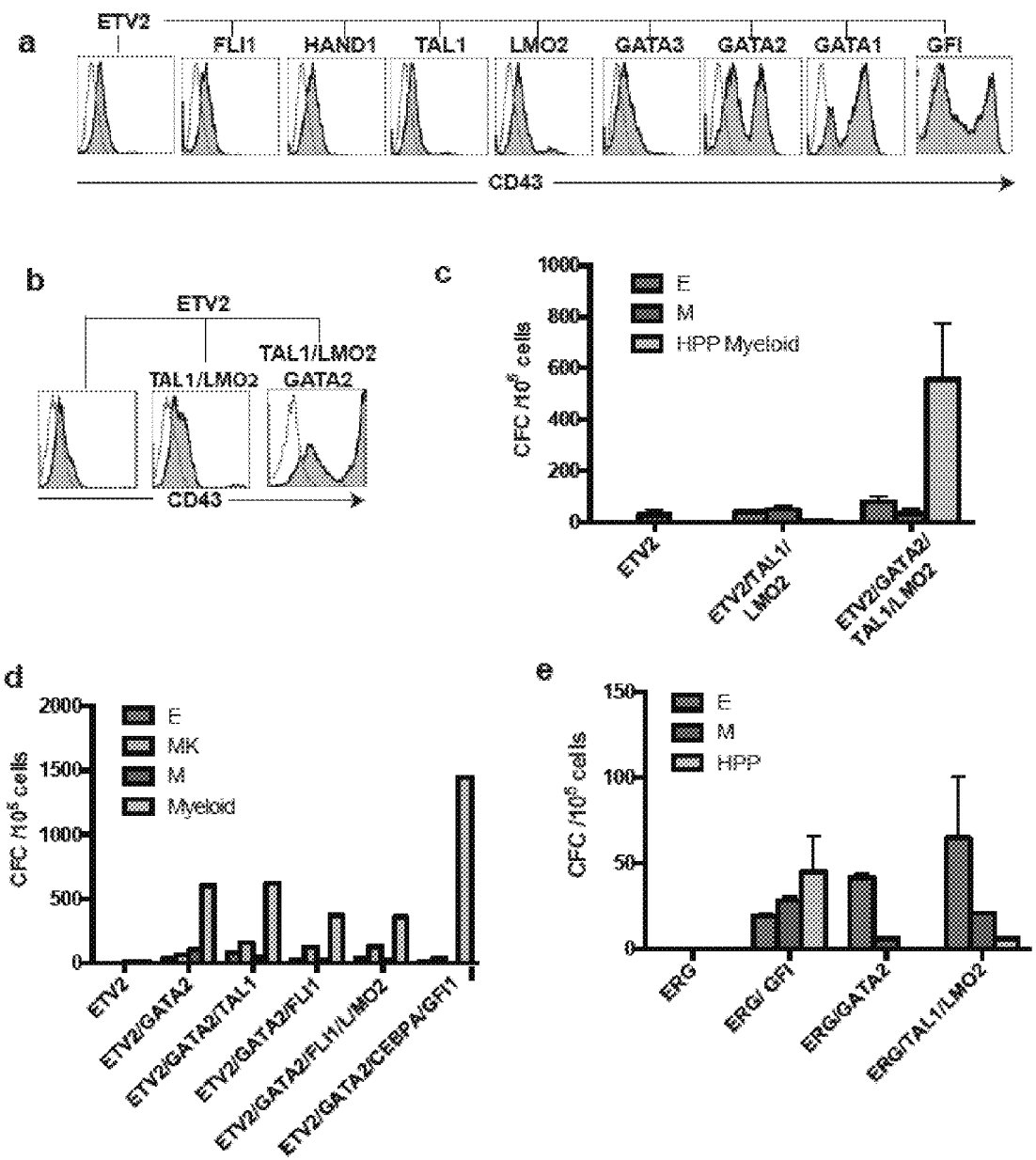
FIG. 8 Screening of different combinations of TFs based on co-expression with ETV2 and ERG. (a) CD43 expression by hESCs on day 7 after transduction with ETV2 plus indicated TFs. (b,c) Advanced hematopoietic programming of cells requires combination of ETV2 with GATA2 but not TAL1 and LMO2 as reflected in the amount of CD43 positive cells on day 7 post-transduction (b), and corresponding colony forming activity (c). (d) Comparative analysis of programming combinations with multiple TFs based on GATA2/ETV2 co-expression. (e) Hematopoietic programming with ERG-based combinations assessed by CFU-assay. Error bars in (c) and (e) show SE from two to four independent experiments. (d) shows results from representative experiment.

Example 2 Overexpression of ETV2 and GATA2 is Sufficient to Induce Pan-Myeloid Hematopoiesis from hESCs Through Hemogenic Endothelium Stage It is generally accepted that blood formation in the embryo proceeds through hemogenic endothelial intermediates. Therefore as a next step we decided to test whether the addition of known hematopoietic factors to ETV2 or ERG endothelium-inductive factors would be sufficient to generate endothelium with hemogenic potential. Given well-established role of GATA2 and GATA1 factors in hematopoietic development and our observation that these factors induce expression of endothelial and hematopoietic genes (FIG. 2a), we selected these TFs as a first choice. In fact, transduction of hESCs with ETV2 and GATA2 led to formation of round CD43 positive blood cells with robust erythroid and myeloid CFC potential (FIGS. 3a and 3b and FIG. 8a). Cells collected from clonogenic cultures of ETV2/GATA2 transduced hESCs robustly proliferated in serum-containing medium with cytokines. Flow cytometric analysis of expansion cultures revealed all types of myeloid cells, including CD34$^+$CD117$^+$ primitive progenitors, CD163$^+$ macrophages, CD66b$^+$ granulocytes, CD41a$^+$ megakaryocytic and CD235a$^+$ erythroid cells indicating that GATA2 and ETV2 induce pan-myeloid hematopoiesis from hESCs (FIG. 3c). GATA1 in combination with ETV2 induced a similar spectrum of hematopoietic colonies, though we noticed an increase in the number of erythroid colonies with GATA1. We also noted that strong induction of CD43$^+$ blood cells could be achieved by co-transfecting hESCs with ETV2 and GFI1 (FIG. 8a). However, these cells demonstrated a very limited erythroid potential and formed mostly granulocytic colonies in clonogenic medium (not shown). Transfection of cells with ETV2 and GATA3, TAL1, or LMO2 induced very few CD43$^+$ cells and much less hematopoietic CFCs as compared with ETV2/GATA2 or GATA1 combination (FIG. 3d and FIG. 8a). The addition of other factors on the top of the ETV2/GATA2 combination did not change substantially the spectrum of hematopoietic programming, although incorporation of erythroid factors TAL1 and LMO2 slightly facilitated the development of erythroid (E) colonies, while GFI1 and CEBPA increased frequency of myeloid progenitors (FIG. 8a-e). We also found that the hematopoietic program can be induced by co-transfecting ERG with GATA2 or GFI1 (FIG. 8e). The number of CFCs induced by these combinations however, was substantially lower compared to GATA2 or GFI1 combined with ETV2.

These observations indicate that co-expression of endothelial factors such as ETV2 or ERG with various GATA2, GATA1, TAL1, or GFI1 TFs leads to induction of hematopoietic program in hESCs with different efficiency and spectrum of clonogenic activity. Because GATA2 and ETV2 combination induced the most robust multi-lineage hematopoiesis, we concluded that these factors are most critical for induction of pan-myeloid hematopoietic program in hESCs.

Gene expression profiling revealed that the combination of ETV2 with GATA2 or GATA1 was sufficient to activate almost the entire spectrum of genes essential for hematopoiesis, including endogenous ETV2 and GATA2, TAL1, LMO2, RUNX1, LYL1, and GFI1 among others (FIG. 2a). Interestingly, following activation of endogenous GATA2 and ETV2 genes, expression of exogenous genes in induced blood cells was dramatically downregulated and was hardly detected by PCR FIGS. 6f and 6g), suggesting that these factors may induce an autoregulatory loop to maintain their expression.

Figure 4:
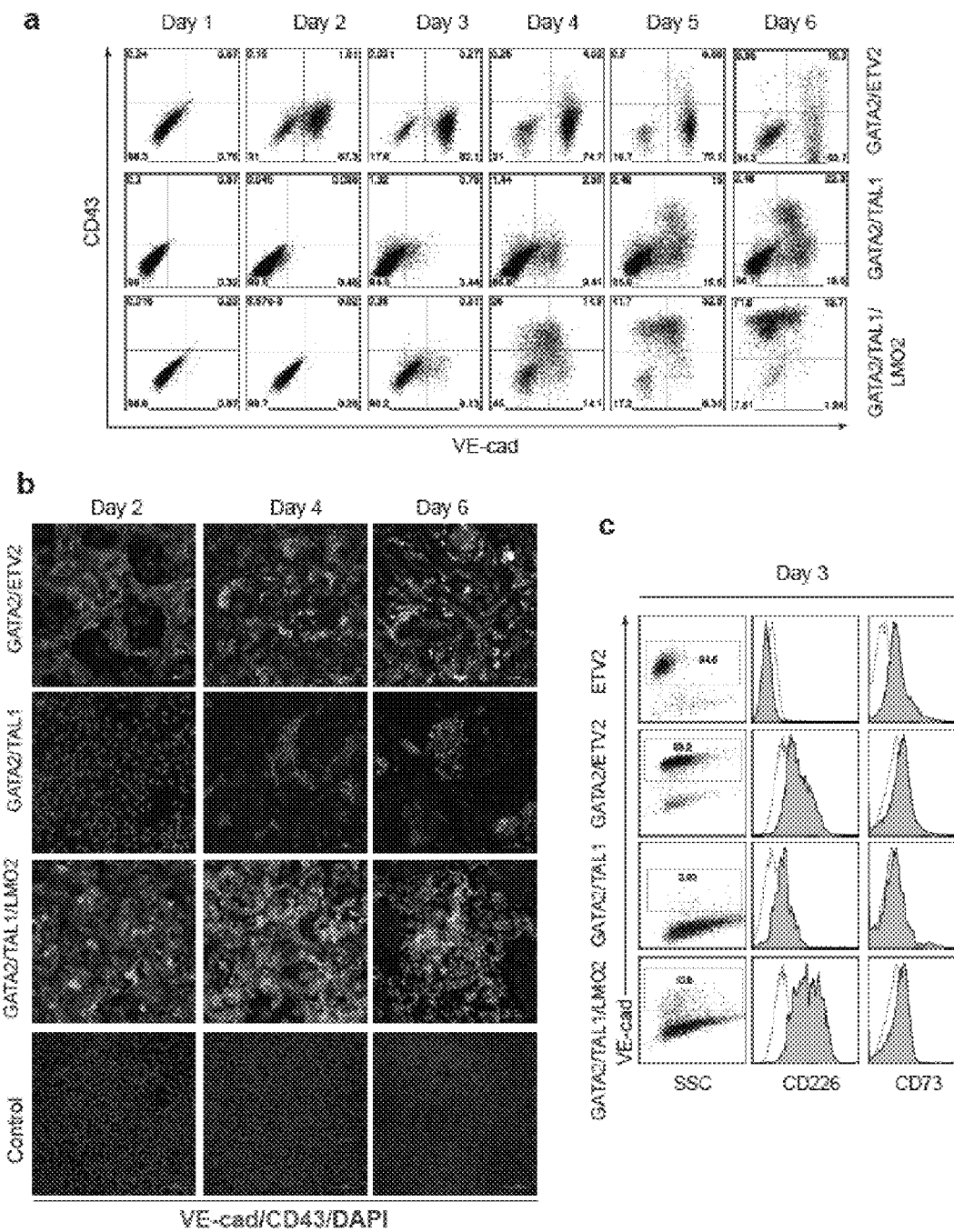
FIG. 4 Direct hematopoietic programming of undifferentiated H1 hESCs goes through an endothelial stage. (a) Kinetic analysis of VE-cadherin and CD43 expression during direct programming of H1 hESCs by GATA2/ETV2, GATA2/TAL1 and GATA2/TAL1/LMO2 TFs by flow cytometry. (b) VE-cadherin and CD43 immunofluorescent staining of untreated control hESCs and hESCs transduced with indicated TFs at different time points after transduction. Scale bars, 100 µm. (c) Expression of markers associated with hemogenic and non-hemogenic endothelium by VE-cadherin+ cells emerging on day 3 post-transduction with indicated TFs.

Kinetic analysis of blood formation by ETV2 and GATA2 transduced cells revealed that hematopoietic development from hESCs proceeds through the endothelial stage. Three days after ETV2 and GATA2 transfection, hESCs acquired typical endothelial morphology and phenotypic features similar to ETV2 transduced hESCs (FIGS. 4a and 4b). However, in contrast to ETV2 alone, endothelial cells induced after 3 days of GATA2 and ETV2 transduction expressed CD226 and lacked CD73 (FIG. 4c), i.e. displayed phenotypic features typical of hemogenic endothelium (10). Within the next two days we observed a transition of endothelial cells into round CD43$^+$ hematopoietic cells, thereby indicating that ETV2 and GATA2 overexpression directly induces formation of endothelial cells with hemogenic properties which subsequently gave rise to blood cells (FIG. 4b). When VE-cadherin$^+$ cells were collected from ETV2/GATA2 transduced cultures prior to detection of CD43 expression (day 3) and cultured on OP9, they generated colonies of CD43$^+$ hematopoietic cells with multilineage CFC potential (FIG. 9a-c), indicating that VE-cadherin$^+$CD43$^-$ cells induced by ETV2/GATA2 have functional potential similar to hemogenic endothelium generated from hESC by differentiation on OP9 (10).

Figure 9:
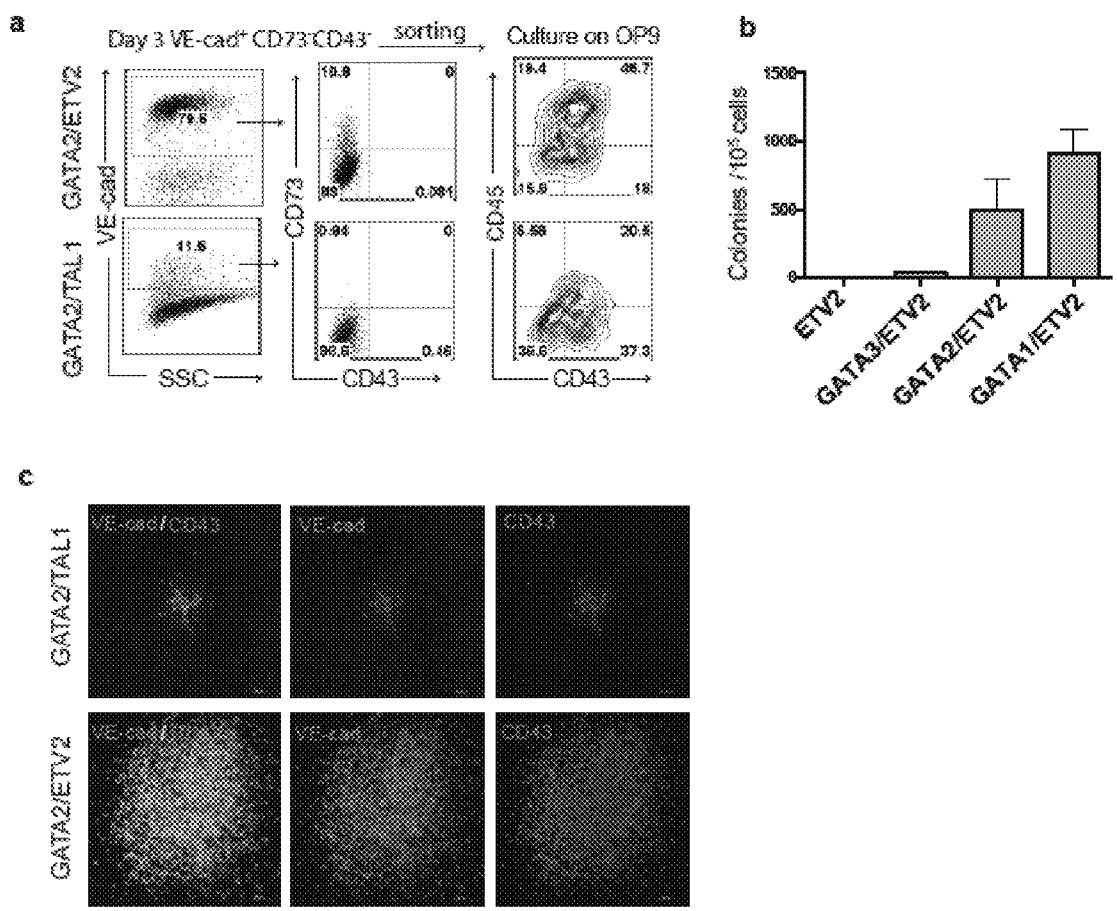
FIG. 9 Hematopoietic potential of VE-cadherin$^+$CD43$^-$CD73$^-$ endothelial cells isolated from programming cultures. (a) On day 3 after transduction with GATA2/ETV2 and GATA2/TAL1, VE-cadherin$^+$CD43$^-$CD73$^-$ cells were isolated by sorting and cultured on OP9 to assess hematopoietic potential. (b) Quantification of clonal hematopoietic clusters developed from VE-cadherin$^+$CD43$^-$CD73$^-$ cells on OP9. Error bar represents 3 independent experiments. (c) Immunofluorescent staining of hematopoietic clusters developed from single VE-cadherin$^+$CD43$^-$CD73$^-$ cells deposited on OP9 monolayer. Scale bar, 100 μm.

Example 3 TAL1 and GATA2 Induce Hematopoietic Program Mostly Restricted to Erythromegakaryocytic Cells Although the basic helix-loop-helix TF TAL1 is a well-known key regulator of hematopoiesis and vasculogenesis (14,15), overexpression of TAL1 alone was not able to induce formation of blood cells from hESCs. When added to ETV2, TAL1 induced only a few hematopoietic colonies (FIG. 3d). Cotransfection of TAL1 with GATA2 or GATA1 genes however, induced the formation of VE-cadherin$^+$ endothelial and CD43$^+$ hematopoietic cells (FIG. 3e) similar to ETV2/GATA2 combination, but in contrast, hematopoiesis in TAL1/GATA2 or GATA1 transduced cultures was predominantly restricted to erythroid and megakaryocytic cells with few macrophages (FIGS. 3f and 3h). Interestingly, the formation of CD43$^+$ round blood cells in cultures was preceded by upregulation of VE-cadherin expression in transformed cells (FIGS. 4a and 4c), indicating that CD43$^+$ cells generated with these two factors, similar to ETV2 and GATA2 transduced cells, arose from endothelial cells through endothelial-hematopoietic transition. Endothelial cells induced by TAL1 and GATA2 on day 3 of culture had phenotypic and functional features of hemogenic endothelium, i.e. they expressed CD226, lacked CD73 (FIG. 4c), and were capable of growing blood after culture on OP9 (FIGS. 9a and 9b). Addition of LMO2 to the TAL1/GATA2 combination dramatically increased hematopoiesis, without significant changes in the spectrum of hematopoietic colonies (FIGS. 3h and 3g). When transcriptional cofactor LMO2 was added to TAL1 and GATA2, we observed rapid transition of hESCs into round CD43$^+$VE-cadherin$^{+/-}$ hematopoietic cells without clearly identifiable preceding endothelial stage.

Figure 10:
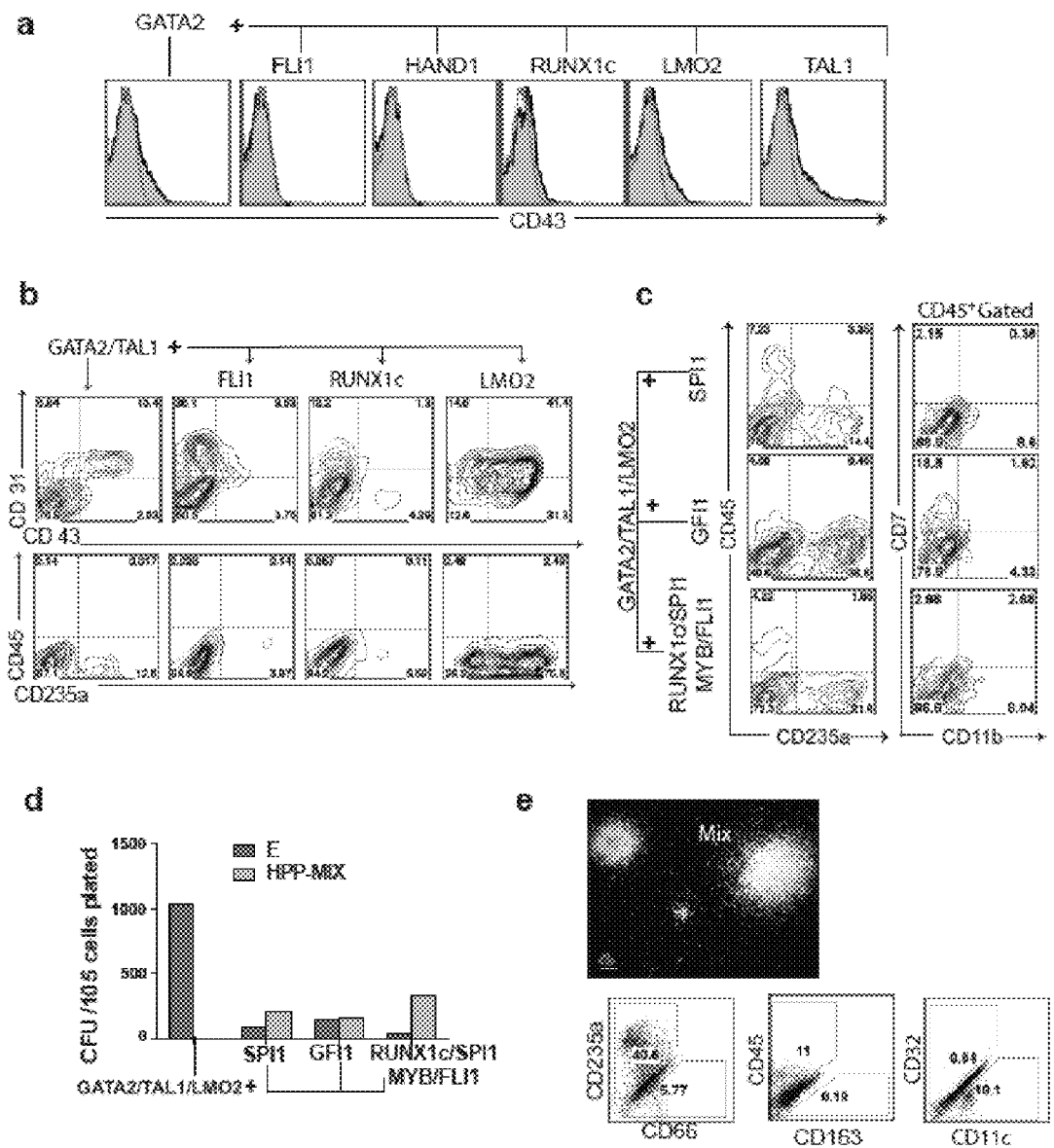
FIG. 10 Screening of different combinations of TFs based on GATA2 and TAL1. (a, b, c) FACS analysis of total cultures collected on day 7 after transduction of hESCs with indicated TFs. (d) Analysis of CFC potential of cells co-expressing erythroid factors (GATA2, TAL1, LMO2) and myeloid factors (SPI1, GFI1, MYB, FLI1, RUNX1C/B). (e) morphology and flow cytometric analysis of colonies formed by hESCs transduced with SPI1, GFI1, MYB, FLI1, RUNX1C/B.

The addition of other factors, including SPI1, and MYB factors that are critical for definitive hematopoiesis, had no significant effect on TAL1/GATA2-induced blood formation and was not able to shift hematopoiesis towards myelomonocytic lineage of cells (FIG. 10b-d). When cells were transfected with a set of seven genes including TAL1, GATA2, LMO2, RUNX1b, RUNX1c, MYB and SPI1, we observed the formation of numerous very large red and white colonies. Cells within these colonies predominantly expressed the erythroid marker CD235a and failed to produce a significant number of myelomonocytic cells (FIG. 10e).

GATA2/TAL1/LMO2 transduced cells collected from clonogenic cultures robustly expanded in serum-free medium with cytokines and generated almost exclusively CD235a$^+$ erythroid and CD41a$^+$ megakaryocytic cells (FIG. 3h), confirming the restricted differentiation potential of cells generated from hESCs using these TFs.

Example 4 Induction of Hematopoietic Program in hiPSCs and by Using Modified mRNA (mmRNA)

Figure 5:
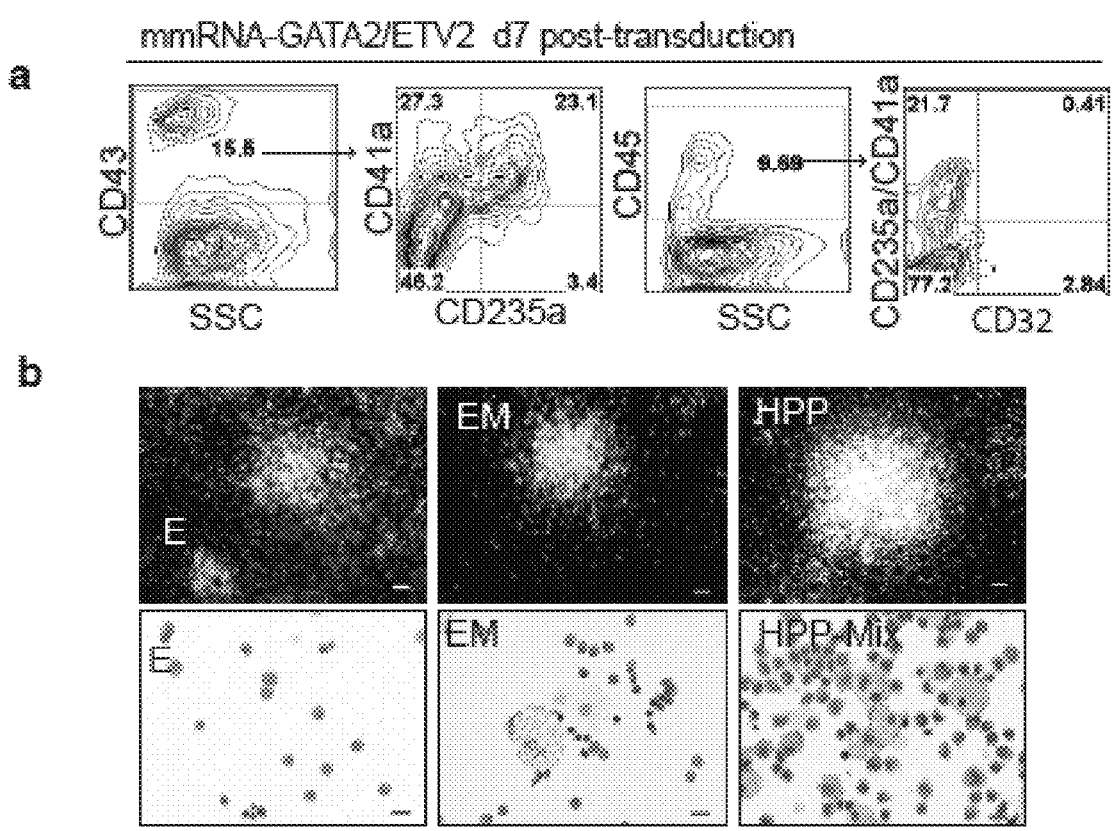
FIG. 5 Hematopoietic induction of hESCs with ETV2/GATA2 mmRNA. (a) Flow cytometric analysis and (b) CFC potential of mmRNA-induced cells.
Figure 11:
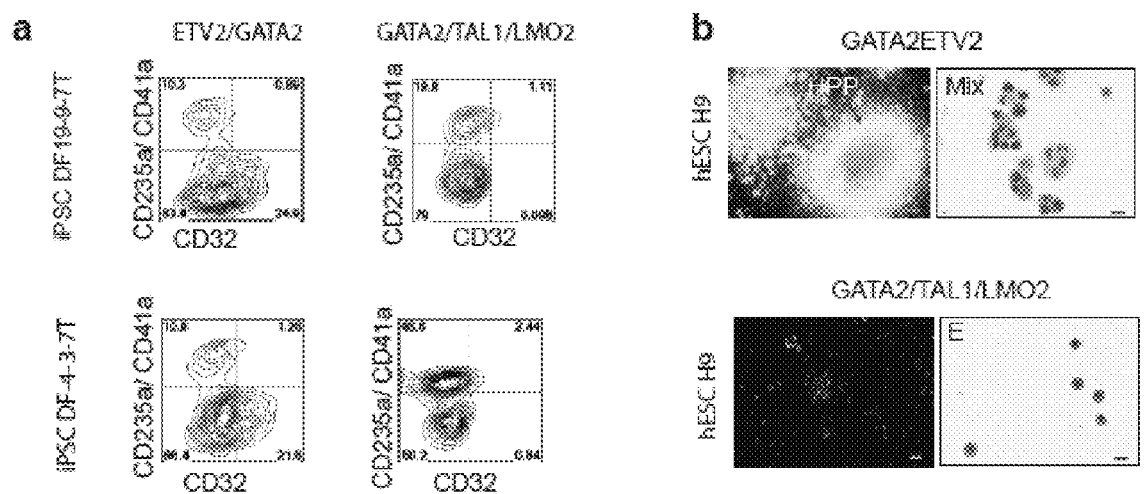
FIG. 11 Hematopoietic programming of H9 hESCs and iPSCs. (a) FACS analysis of TFs differentiated iPS cell lines DF-19-9-7T and DF-4-3-7T grown in low attachment conditions in the presence of cytokines and 10% FBS. (b) Colony forming units developed from H9 hESCs by induction of GATA2/ETV2 and GATA2/TAL1/LMO2.

To determine whether the identified sets of transcriptional regulators were capable of inducing the hematopoietic program in hPSCs other than H1 hESCs, we overexpressed ETV2/GATA2 or TAL1/GATA2/LMO2 in two fibroblast-derived iPSCs. As shown in FIG. 11, hematopoiesis induced using these combinations in hiPSCs was similar to what we observed with H1 hESCs. i.e. ETV2 and GATA2 induced pan-myeloid hematopoiesis, while the TAL1/GATA2/LMO2 combination induced predominantly the erythroid and megakaryocytic cells. Pan-myeloid program in hESCs was successfully induced by mmRNA indicating that short exposure to TFs is sufficient for the induction of the hematopoietic program (FIG. 5).

Using a gain-of-function genetic screen we identified ETV2 and GATA2 as the most critical TFs required for induction of hemogenic endothelium with pan-myeloid potential from hESCs. ETV2 and ERG are ETS family of TFs which play critical roles in endothelial development (16). Gain-of-function experiments in *Xenopus* and zebrafish embryos have demonstrated that ERG and ETV2 are able to induce ectopic endothelial differentiation (17-19). ETV2 is also required for HSC development from hemogenic endothelium and the maintenance of adult HSCs (20, 21). We found that ectopic expression of ETV2 and ERG in undifferentiated hESCs upregulated expression of genes associated with angiohematopoietic development and typical endothelial genes resulting in the formation of endothelial cells. Although overexpression of ETV2 alone induced expression of endogenous FLI1, GATA2, and TAL1, genes which form the core of a gene regulatory network in developing HSCs (22), ETV2-induced endothelium was lacking significant blood-forming activity. The overexpression of GATA2 or GATA1 in addition to ETV2 was required to achieve induction of hemogenic endothelial cells and the formation of multipotential hematopoietic progenitors. These findings indicated that ETV2 and GATA2 act at the top of the transcriptional network driving the endothelial and myeloid development from hESCs.

Mouse studies have demonstrated that Tal1 controls the expression of several important hematopoietic regulators, including Runx1, Erg, Gfi1b, and Gata2 among others (23). Tal1 is considered a key component of the regulatory network controlling HSC specification (22). However, TAL1 overexpression in hESCs induced only minimal changes in the gene expression profile indicating that TAL1 target genes in undifferentiated cells may not have open chromatin structure for access by TAL1. The cotransfection of TAL1 with GATA1 or GATA2 TFs was sufficient to induce hemogenic endothelium, which in contrast to ETV2/GATA2 or ETV2/GATA1-induced endothelium had restricted erythromegakaryocytic and macrophage potential. While hematopoiesis induced by TAL1 and GATA1 or GATA2 TFs was relatively weak, additional transduction of cells with LMO2 transcriptional cofactor led to robust formation of blood cells of the erythromegakaryocytic lineage.

Overall, our studies identified two critical pathways leading to the formation of distinct types of hemogenic endothelium and have provided a novel platform to assess the hematopoietic transcriptional program in hPSCs required for HSC induction. Additionally, these studies offer a novel approach to induce efficient production of endothelium and blood from hPSCs by forced expression of transcription factors.

REFERENCES

1. Davidson E H. (2010). Emerging properties of animal gene regulatory networks. Nature 468:911-20.
2. Godin I and A Cumano. (2002). The hare and the tortoise: an embryonic haematopoietic race. Nat Rev Immunol 2:593-604.
3. Lessard J, A Faubert and G Sauvageau. (2004). Genetic programs regulating HSC specification, maintenance and expansion. Oncogene 23:7199-209.
4. Teitell M A and H K Mikkola. (2006). Transcriptional activators, repressors, and epigenetic modifiers controlling hematopoietic stem cell development. Pediatric research 59:33R-9R.
5. Wilson N K, F J Calero-Nieto, R Ferreira and B Gottgens. (2011). Transcriptional regulation of haematopoietic transcription factors. Stem cell research & therapy 2:6.
6. Donaldson I J, M Chapman, S Kinston, J R Landry, K Knezevic, S Piltz, N Buckley, A R Green and B Gottgens. (2005). Genome-wide identification of cis-regulatory sequences controlling blood and endothelial development. Hum Mol Genet 14:595-601. Epub 2005 Jan. 13.
7. Boisset J C, W van Cappellen, C Andrieu-Soler, N Galjart, E Dzierzak and C Robin. (2010). In vivo imaging of haematopoietic cells emerging from the mouse aortic endothelium. Nature 464:116-20.
8. Zovein A C, J J Hofmann, M Lynch, W J French, K A Turlo, Y Yang, M S Becker, L Zanetta, E Dejana, J C Gasson, M D Tallquist and M L Iruela-Arispe. (2008). Fate tracing reveals the endothelial origin of hematopoietic stem cells. Cell Stem Cell 3:625-36.

9. Jaffredo T, R Gautier, V Brajeul and F Dieterlen-Lievre. (2000). Tracing the progeny of the aortic hemangioblast in the avian embryo. Dev Biol 224:204-14.
10. Choi K D, M A Vodyanik, P P Togarrati, K Suknuntha, A Kumar, F Samarjeet, M D Probasco, S Tian, R Stewart, J A Thomson and Slukvin, I I. (2012). Identification of the hemogenic endothelial progenitor and its direct precursor in human pluripotent stem cell differentiation cultures. Cell Reports 2:553-67.
11. Vodyanik M A, J Yu, X Zhang, S Tian, R Stewart, J A Thomson and Slukvin, I I. (2010). A mesoderm-derived precursor for mesenchymal stem and endothelial cells. Cell Stem Cell 7:718-29.
12. Mahlapuu M, M Ormestad, S Enerback and P Carlsson. (2001). The forkhead transcription factor Foxf1 is required for differentiation of extra-embryonic and lateral plate mesoderm. Development 128:155-66.
13. Barnes R M, B A Firulli, S J Conway, J W Vincentz and A B Firulli. (2010). Analysis of the Hand1 cell lineage reveals novel contributions to cardiovascular, neural crest, extra-embryonic, and lateral mesoderm derivatives. Developmental dynamics: an official publication of the American Association of Anatomists 239:3086-97.
14. Robb L, N J Elwood, A G Elefanty, F Kontgen, R Li, L D Barnett and C G Begley. (1996). The scl gene product is required for the generation of all hematopoietic lineages in the adult mouse. Embo J 15:4123-9.
15. Visvader J E, Y Fujiwara and S H Orkin. (1998). Unsuspected role for the T-cell leukemia protein SCL/tal-1 in vascular development. Genes Dev 12:473-9.
16. Meadows S M, C T Myers and P A Krieg. (2011). Regulation of endothelial cell development by ETS transcription factors. Seminars in cell & developmental biology 22:976-84.
17. Baltzinger M, A M Mager-Heckel and P Remy. (1999). X1 erg: expression pattern and overexpression during development plead for a role in endothelial cell differentiation. Developmental dynamics: an official publication of the American Association of Anatomists 216:420-33.
18. Wong K S, K Proulx, M S Rost and S Sumanas. (2009). Identification of vasculature-specific genes by microarray analysis of Etsrp/Etv2 overexpressing zebrafish embryos. Developmental dynamics: an official publication of the American Association of Anatomists 238:1836-50.
19. Neuhaus H, F Muller and T Hollemann. (2010). Xenopus er71 is involved in vascular development. Developmental dynamics: an official publication of the American Association of Anatomists 239:3436-45.
20. Ren X, G A Gomez, B Zhang and S Lin. (2010). Scl isoforms act downstream of etsrp to specify angioblasts and definitive hematopoietic stem cells. Blood 115:5338-46.
21. Lee D, T Kim and D S Lim. (2011). The Er71 is an important regulator of hematopoietic stem cells in adult mice. Stem Cells 29:539-48.
22. Pimanda J E, K Ottersbach, K Knezevic, S Kinston, W Y Chan, N K Wilson, J R Landry, A D Wood, A Kolb-Kokocinski, A R Green, D Tannahill, G Lacaud, V Kouskoff and B Gottgens. (2007). Gata2, Fli1, and Scl form a recursively wired gene-regulatory circuit during early hematopoietic development. Proc Natl Acad Sci USA 104:17692-7. Epub 2007 Oct. 25.
23. Wilson N K, D Miranda-Saavedra, S Kinston, N Bonadies, S D Foster, F Calero-Nieto, M A Dawson, I J Donaldson, S Dumon, J Frampton, R Janky, X H Sun, A Teichmann, A J Bannister and B Gottgens. (2009). The transcriptional program controlled by the stem cell leukemia gene Scl/Tal1 during early embryonic hematopoietic development. Blood 113:5456-65.
24. Yokomizo T and E Dzierzak. (2010). Three-dimensional cartography of hematopoietic clusters in the vasculature of whole mouse embryos. Development 137:3651-61.
25. Gekas C, F Dieterlen-Lievre, S H Orkin and H K Mikkola. (2005). The placenta is a niche for hematopoietic stem cells. Dev Cell 8:365-75.
26. Li Z, Y Lan, W He, D Chen, J Wang, F Zhou, Y Wang, H Sun, X Chen, C Xu, S Li, Y Pang, G Zhang, L Yang, L Zhu, M Fan, A Shang, Z Ju, L Luo, Y Ding, W Guo, W Yuan, X Yang and B Liu. (2012). Mouse embryonic head as a site for hematopoietic stem cell development. Cell Stem Cell 11:663-75.
27. Nakano H, X Liu, A Arshi, Y Nakashima, B van Handel, R Sasidharan, A W Harmon, J H Shin, R J Schwartz, S J Conway, R P Harvey, M Pashmforoush, H K Mikkola and A Nakano. (2013). Haemogenic endocardium contributes to transient definitive haematopoiesis. Nature communications 4:1564.
28. Li W, M J Ferkowicz, S A Johnson, W C Shelley and M C Yoder. (2005). Endothelial cells in the early murine yolk sac give rise to CD41-expressing hematopoietic cells. Stem Cells Dev 14:44-54.
29. Taoudi S and A Medvinsky. (2007). Functional identification of the hematopoietic stem cell niche in the ventral domain of the embryonic dorsal aorta. Proc Natl Acad Sci USA 104:9399-403.
30. Chen M J, Y Li, M E De Obaldia, Q Yang, A D Yzaguirre, T Yamada-Inagawa, C S Vink, A Bhandoola, E Dzierzak and N A Speck. (2011). Erythroid/myeloid progenitors and hematopoietic stem cells originate from distinct populations of endothelial cells. Cell Stem Cell 9:541-52.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

APPENDIX

Amino Acid Sequences of IFs (SEQ ID NOs: 1-7)
(DNA binding domains are underlined)

ETV2

(SEQ ID NO: 1)

MDLWNWDEASPQEVPPGNKLAGLEGAKLGFCFPDLALQGDTPTATAET

CWKGTSSSLASFPQLDWGSALLHPEVPWGAEPDSQALPWSGDWTDMAC

TAWDSWSGASQTLGPAPLGPGPIPAAGSEGAAGQNCVPVAGEATSWSR

AQAAGSNTSWDCSVGPDGDTYWGSGLGGEPRTDCTISWGGPAGPDCTT

SWNPGLHAGGTTSLKRYQSSALTVCSEPSPQSDRASLARCPKTNHRG<u>P</u>

<u>IQLWQFLLELLHDGARSSCIRWTGNSREFQLCDPKEVARLWGERKRKP</u>

<u>GMNYEKLSRGLRYYYRRDIVRKSGGRKYTYRF</u>GGRVPSLAYPDCAGGG

RGAETQ

APPENDIX-continued

Amino Acid Sequences of IFs (SEQ ID NOs: 1-7)
(DNA binding domains are underlined)

GATA1
(SEQ ID NO: 2)
MEFPGLGSLGTSEPLPQFVDPALVSSTPESGVFFPSGPEGLDAAASST
APSTATAAAALAYYRDAEAYRHSPVFQVYPLLNCMEGIPGGSPYAGW
AYGKTGLYPASTVCPTREDSPPQAVEDLDGKGSTSFLETLKTERLSPD
LLTLGPALPSSLPVPNSAYGGPDFSSTFFSPTGSPLNSAAYSSPKLRG
TLPLPPCEARE<u>CVNCGATATPLWRRDRTGHYLCNAC</u>GLYHKMNGQNRP
LIRPKKRLIVSKRAGTQ<u>CTNCQTTTTTLWRRNASGDPVCNAC</u>GLYYKL
HQVNRPLTMRKDGIQTRNRKASGKGKKKRGSSLGGTGAAEGPAGGFMV
VAGGSGSGNCGEVASGLTLGPPGTAHLYQGLGPVVLSGPVSHLMPFPG
PLLGSPTGSFPTGPMPPTTSTTVVAPLSS

ERG
(SEQ ID NO: 3)
MIQTVPDPAAHIKEALSVVSEDQSLFECAYGTPHLAKTEMTASSSSDY
GQTSKMSPRVPQQDWLSQPPARVTIKMECNPSQVNGSRNSPDECSVAK
GGKMVGSPDTVGMNYGSYMEEKHMPPPNMTTNERRVIVPADPTLWSTD
HVRQWLEWAVKEYGLPDVNILLFQNIDGKELCKMTKDDFQRLTPSYNA
DILLSHLHYLRETPLPHLTSDDVDKALQNSPRLMHARNTGGAAFIFPN
TSVYPEATQRITTRPDLPYEPPRRSAWTGHGHPTPQSKAAQPSPSTVP
KTEDQRPQLDPYQILGPTSSRLANPGSGQ<u>IQLWQFLLELLSDSSNSSC
ITWEGTNGEFKMTDPDEVARRWGERKSKPNMNYDKLSRALRYYYDKNI
MTKVHGKRYAYKFD</u>FHGIAQALQPHPPESSLYKYPSDLPYMGSYHAHP
QKMNFVAPHPPALPVTSSSFFAAPNPYWNSPTGGIYPNTRLPTSHMPS
HLGTYY

GATA2
(SEQ ID NO: 4)
MEVAPEQPRWMAHPAVLNAQHPDSHHPGLAHNYMEPAQLLPPDEVDVF
FNHLDSQGNPYYANPAHARARVSYSPAHARLTGGQMCRPHLLHSPGLP
WLDGGKAALSAAAAHHHNPWTVSPFSKTPLHPSAAGGPGGPLSVYPGA
GGGSGGGSGSSVASLTPTAAHSGSHLFGFPPTPPKEVSPDPSTTGAAS
PASSSAGGSAARGEDKDGVKYQVSLTESMKMESGSPLRPGLATMGTQP

ATHHPIPTYPSYVPAAAHDYSSGLFHPGGFLGGPASSFTPKQRSKARS
CSEGRE<u>CVNCGATATPLWRRDGTGHYLCNAC</u>GLYHKMNGQNRPLIKPK
RRLSAARRAGTC<u>CANCQTTTTTLWRRNANGDPVCNAC</u>GLYYKLHNVNR
PLTMKKEGIQTRNRKMSNKSKKSKKGAECFEELSKCMQEKSSPFSAAA
LAGHMAPVGHLPPFSHSGHILPTPTPIHPSSSLSFGHPHPSSMVTAMG

GFI1
(SEQ ID NO: 5)
MPRSFLVKSKKAHSYHQPRSPGPDYSLRLENVPAPSRADSTSNAGGAK
AEPRDRLSPESQLTEAPDRASASPDSCEGSVCERSSEFEDFWRPPSPS
ASPASEKSMCPSLDEAQPFPLPFKPYSWSGLAGSDLRHLVQSYRPCGA
LERGAGLGLFCEPAPEPGHPAALYGPKRAAGGAGAGAPGSCSAGAGAT
AGPGLGLYGDFGSAAAGLYERPTAAAGLLYPERGHGLHADKGAGVKVE
SELLCTRLLLGGGS<u>YKCIKCSKVFSTPHGLEVHVRRSHSGTRPFACEM
CGKTFGHAVSLEQHKAVHSQERSFDCKICGKSFKRSSTLSTHLLIHSD
TRPYPCQYCGKRFHQKSDMKKHTFIHTGEKPHKCQVCGKAFSQSSNLI
THSRKHTGFKPFGCDLCGKGFQRKVDLRRHRETQHGLK</u>

TAL1
(SEQ ID NO: 6)
MTERPPSEAARSDPQLEGRDAAEASMAPPHLVLLNGVAKETSRAAAAE
PPVIELGARGGPGGGPAGGGGAARDLKGRDAATAEARHRVPTTELCRP
PGPAPAPAPASVTAELPGDGRMVQLSPPALAAPAAPGRALLYSLSQPL
ASLGSGFFGEPDAFPMFTTNNRVKRRPSPYEMEITDGPHTKV<u>VRRIFT
NSRERWRQQNVNGAFAELRKLIPTHPPDKKLSKNEILRLAMKYINFLA
KLLNDQEEEGTQRAKTGKDPVVGAGGGGGGGGGAPPDDLLQDVLSPN
SSCGSSLDGAASPDSYTEEPAPKHTARSLHPAMLPAADGAGPR

LMO2
(SEQ ID NO: 7)
MSSAIERKSLDPSEEPVDEVLQIPPSLLTCGGCQQNIGDRYFLKAIDQ
YWHEDCLSCDLCGCRLGEVGRRLYYKLGRKLCRRDYLRLFGQDGLCAS
CDKRIRAYEMTMRVKDKVYHLECFKCAACQKHFCVGDRYLLINSDIVC
EQDIYEWTKINGMI

---

We claim:

1. A kit for hemogenic reprogramming, comprising:
one or more recombinant expression viruses comprising a nucleic acid encoding an ETV2 or ERG protein, and a GATA1 protein.

2. The kit of claim 1, wherein the ETV2, ERG, or GATA1 sequence are from human, mouse, or rat.

3. A kit for hemogenic reprogramming, comprising:
one or more isolated modified mRNAs comprising an open reading frame for ETV2 or ERG, and GATA1, wherein the modified mRNA comprises:
a 5' synthetic cap;
modified nucleotides, wherein the modified nucleotides comprise a member selected form the group consisting of pseudo-uridine and 5-methyl-cytosine; and
a 3' poly-A tail.

4. The kit of claim 3, wherein the 5' synthetic cap is methylated.

5. A kit for hemogenic reprogramming, comprising:
one or more isolated modified mRNAs comprising an open reading frame from ETV2 or ERG, and GATA1, wherein the modified mRNA comprises:
a 5' synthetic cap;
modified nucleotides; and
a poly-A tail, wherein the modified mRNA comprises 3'-O-Me-m7G(5')pp(5')G.

6. The kit of claim 1, wherein the ETV2 protein comprises SEQ ID NO:1.

7. The kit of claim 1, wherein the ERG protein comprises SEQ ID NO:3.

8. The kit of claim 1, wherein the GATA protein comprises SEQ ID NO:2.

9. A kit for hemogenic reprogramming, comprising:
one or more double stranded DNA expression vectors comprising a heterologous nucleic acid sequence encoding an ETV2 or ERG protein and a GATA1 protein.

10. The kit of claim 9, wherein the ETV2, ERG, or GATA1 sequence are from human, mouse, or rat.

11. The kit of claim 9, wherein the ETV2 protein comprises SEQ ID NO:1.

12. The kit of claim 9, wherein the ERG protein comprises SEQ ID NO:3.

13. The kit of claim 9, wherein the GATA protein comprises SEQ ID NO:2.

14. The kit of claim 1, wherein the ETV2, ERG, or GATA1 sequence are from human, mouse, or rat.

15. The kit of claim 3, wherein the ETV2 protein comprises SEQ ID NO:1.

16. The kit of claim 3, wherein the ERG protein comprises SEQ ID NO:3.

17. The kit of claim 3, wherein the GATA protein comprises SEQ ID NO:2.

18. The kit of claim 5, wherein the ETV2, ERG, or GATA1 sequence are from human, mouse, or rat.

19. The kit of claim 5, wherein the ETV2 protein comprises SEQ ID NO:1.

20. The kit of claim 5, wherein the ERG protein comprises SEQ ID NO:3.

21. The kit of claim 5, wherein the GATA protein comprises SEQ ID NO:2.

* * * * *

UNITED STATES PATENT AND TRADEMARK OFFICE
CERTIFICATE OF CORRECTION

| | | |
|---|---|---|
| PATENT NO. | : 9,765,327 B2 | Page 1 of 1 |
| APPLICATION NO. | : 15/183191 | |
| DATED | : September 19, 2017 | |
| INVENTOR(S) | : Slukvin et al. | |

It is certified that error appears in the above-identified patent and that said Letters Patent is hereby corrected as shown below:

In the Specification

Column 9, Line 1, "at" should be --al--.

In the Claims

Column 45, Claim 3, Line 30, "form" should be --from--.

Signed and Sealed this
Sixteenth Day of July, 2019

Andrei Iancu
*Director of the United States Patent and Trademark Office*

SEQUENCE LISTING

<160> NUMBER OF SEQ ID NOS: 13

<210> SEQ ID NO 1
<211> LENGTH: 342
<212> TYPE: PRT
<213> ORGANISM: HUMAN

<400> SEQUENCE: 1

Met Asp Leu Trp Asn Trp Asp Glu Ala Ser Pro Gln Glu Val Pro Pro
1               5                   10                  15

Gly Asn Lys Leu Ala Gly Leu Glu Gly Ala Lys Leu Gly Phe Cys Phe
            20                  25                  30

Pro Asp Leu Ala Leu Gln Gly Asp Thr Pro Thr Ala Thr Ala Glu Thr
                35                  40                  45

Cys Trp Lys Gly Thr Ser Ser Leu Ala Ser Phe Pro Gln Leu Asp
 50                  55                  60

Trp Gly Ser Ala Leu Leu His Pro Glu Val Pro Trp Gly Ala Glu Pro
 65                  70                  75                  80

Asp Ser Gln Ala Leu Pro Trp Ser Gly Asp Trp Thr Asp Met Ala Cys
                85                  90                  95

Thr Ala Trp Asp Ser Trp Ser Gly Ala Ser Gln Thr Leu Gly Pro Ala
               100                 105                 110

Pro Leu Gly Pro Gly Pro Ile Pro Ala Ala Gly Ser Glu Gly Ala Ala
               115                 120                 125

Gly Gln Asn Cys Val Pro Val Ala Gly Glu Ala Thr Ser Trp Ser Arg
130                 135                 140

Ala Gln Ala Ala Gly Ser Asn Thr Ser Trp Asp Cys Ser Val Gly Pro
145                 150                 155                 160

Asp Gly Asp Thr Tyr Trp Gly Ser Gly Leu Gly Gly Glu Pro Arg Thr
                165                 170                 175

Asp Cys Thr Ile Ser Trp Gly Gly Pro Ala Gly Pro Asp Cys Thr Thr
                180                 185                 190

Ser Trp Asn Pro Gly Leu His Ala Gly Thr Thr Ser Leu Lys Arg
                195                 200                 205

Tyr Gln Ser Ser Ala Leu Thr Val Cys Ser Glu Pro Ser Pro Gln Ser
    210                 215                 220

Asp Arg Ala Ser Leu Ala Arg Cys Pro Lys Thr Asn His Arg Gly Pro
225                 230                 235                 240

Ile Gln Leu Trp Gln Phe Leu Leu Glu Leu Leu His Asp Gly Ala Arg
                245                 250                 255

Ser Ser Cys Ile Arg Trp Thr Gly Asn Ser Arg Glu Phe Gln Leu Cys
                260                 265                 270

Asp Pro Lys Glu Val Ala Arg Leu Trp Gly Glu Arg Lys Arg Lys Pro
                275                 280                 285

Gly Met Asn Tyr Glu Lys Leu Ser Arg Gly Leu Arg Tyr Tyr Tyr Arg
                290                 295                 300

Arg Asp Ile Val Arg Lys Ser Gly Gly Arg Lys Tyr Thr Tyr Arg Phe
305                 310                 315                 320

Gly Gly Arg Val Pro Ser Leu Ala Tyr Pro Asp Cys Ala Gly Gly Gly
                325                 330                 335

Arg Gly Ala Glu Thr Gln
            340

<210> SEQ ID NO 2
<211> LENGTH: 413
<212> TYPE: PRT
<213> ORGANISM: HUMAN

<400> SEQUENCE: 2

Met Glu Phe Pro Gly Leu Gly Ser Leu Gly Thr Ser Glu Pro Leu Pro
1               5                   10                  15

Gln Phe Val Asp Pro Ala Leu Val Ser Ser Thr Pro Glu Ser Gly Val
                20                  25                  30

Phe Phe Pro Ser Gly Pro Glu Gly Leu Asp Ala Ala Ser Ser Ser Thr
                35                  40                  45

Ala Pro Ser Thr Ala Thr Ala Ala Ala Ala Leu Ala Tyr Tyr Arg

```
                 50                  55                  60
Asp Ala Glu Ala Tyr Arg His Ser Pro Val Phe Gln Val Tyr Pro Leu
 65                  70                  75                  80

Leu Asn Cys Met Glu Gly Ile Pro Gly Gly Ser Pro Tyr Ala Gly Trp
                 85                  90                  95

Ala Tyr Gly Lys Thr Gly Leu Tyr Pro Ala Ser Thr Val Cys Pro Thr
                100                 105                 110

Arg Glu Asp Ser Pro Pro Gln Ala Val Glu Asp Leu Asp Gly Lys Gly
                115                 120                 125

Ser Thr Ser Phe Leu Glu Thr Leu Lys Thr Glu Arg Leu Ser Pro Asp
                130                 135                 140

Leu Leu Thr Leu Gly Pro Ala Leu Pro Ser Ser Leu Pro Val Pro Asn
145                 150                 155                 160

Ser Ala Tyr Gly Gly Pro Asp Phe Ser Ser Thr Phe Phe Ser Pro Thr
                165                 170                 175

Gly Ser Pro Leu Asn Ser Ala Ala Tyr Ser Ser Pro Lys Leu Arg Gly
                180                 185                 190

Thr Leu Pro Leu Pro Pro Cys Glu Ala Arg Glu Cys Val Asn Cys Gly
                195                 200                 205

Ala Thr Ala Thr Pro Leu Trp Arg Arg Asp Arg Thr Gly His Tyr Leu
                210                 215                 220

Cys Asn Ala Cys Gly Leu Tyr His Lys Met Asn Gly Gln Asn Arg Pro
225                 230                 235                 240

Leu Ile Arg Pro Lys Lys Arg Leu Ile Val Ser Lys Arg Ala Gly Thr
                245                 250                 255

Gln Cys Thr Asn Cys Gln Thr Thr Thr Thr Thr Leu Trp Arg Arg Asn
                260                 265                 270

Ala Ser Gly Asp Pro Val Cys Asn Ala Cys Gly Leu Tyr Tyr Lys Leu
                275                 280                 285

His Gln Val Asn Arg Pro Leu Thr Met Arg Lys Asp Gly Ile Gln Thr
                290                 295                 300

Arg Asn Arg Lys Ala Ser Gly Lys Gly Lys Lys Lys Arg Gly Ser Ser
305                 310                 315                 320

Leu Gly Gly Thr Gly Ala Ala Glu Gly Pro Ala Gly Gly Phe Met Val
                325                 330                 335

Val Ala Gly Gly Ser Gly Ser Gly Asn Cys Gly Glu Val Ala Ser Gly
                340                 345                 350

Leu Thr Leu Gly Pro Pro Gly Thr Ala His Leu Tyr Gln Gly Leu Gly
                355                 360                 365

Pro Val Val Leu Ser Gly Pro Val Ser His Leu Met Pro Phe Pro Gly
                370                 375                 380

Pro Leu Leu Gly Ser Pro Thr Gly Ser Phe Pro Thr Gly Pro Met Pro
385                 390                 395                 400

Pro Thr Thr Ser Thr Thr Val Val Ala Pro Leu Ser Ser
                405                 410
```

<210> SEQ ID NO 3
<211> LENGTH: 486
<212> TYPE: PRT
<213> ORGANISM: HUMAN

<400> SEQUENCE: 3

```
Met Ile Gln Thr Val Pro Asp Pro Ala Ala His Ile Lys Glu Ala Leu
  1               5                  10                  15
```

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Asp Tyr
                35                  40                  45

Gly Gln Thr Ser Lys Met Ser Pro Arg Val Pro Gln Gln Asp Trp Leu
 50                  55                  60

Ser Gln Pro Pro Ala Arg Val Thr Ile Lys Met Glu Cys Asn Pro Ser
65                   70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
                100                 105                 110

Ser Tyr Met Glu Glu Lys His Met Pro Pro Asn Met Thr Thr Asn
            115                 120                 125

Glu Arg Arg Val Ile Val Pro Ala Asp Pro Thr Leu Trp Ser Thr Asp
            130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
            195                 200                 205

His Leu Thr Ser Asp Asp Val Asp Lys Ala Leu Gln Asn Ser Pro Arg
210                 215                 220

Leu Met His Ala Arg Asn Thr Gly Gly Ala Ala Phe Ile Phe Pro Asn
225                 230                 235                 240

Thr Ser Val Tyr Pro Glu Ala Thr Gln Arg Ile Thr Thr Arg Pro Asp
                245                 250                 255

Leu Pro Tyr Glu Pro Pro Arg Arg Ser Ala Trp Thr Gly His Gly His
                260                 265                 270

Pro Thr Pro Gln Ser Lys Ala Ala Gln Pro Ser Pro Ser Thr Val Pro
            275                 280                 285

Lys Thr Glu Asp Gln Arg Pro Gln Leu Asp Pro Tyr Gln Ile Leu Gly
            290                 295                 300

Pro Thr Ser Ser Arg Leu Ala Asn Pro Gly Ser Gly Gln Ile Gln Leu
305                 310                 315                 320

Trp Gln Phe Leu Leu Glu Leu Leu Ser Asp Ser Ser Asn Ser Ser Cys
                325                 330                 335

Ile Thr Trp Glu Gly Thr Asn Gly Glu Phe Lys Met Thr Asp Pro Asp
                340                 345                 350

Glu Val Ala Arg Arg Trp Gly Glu Arg Lys Ser Lys Pro Asn Met Asn
            355                 360                 365

Tyr Asp Lys Leu Ser Arg Ala Leu Arg Tyr Tyr Asp Lys Asn Ile
            370                 375                 380

Met Thr Lys Val His Gly Lys Arg Tyr Ala Tyr Lys Phe Asp Phe His
385                 390                 395                 400

Gly Ile Ala Gln Ala Leu Gln Pro His Pro Glu Ser Ser Leu Tyr
                405                 410                 415

Lys Tyr Pro Ser Asp Leu Pro Tyr Met Gly Ser Tyr His Ala His Pro
            420                 425                 430

Gln Lys Met Asn Phe Val Ala Pro His Pro Pro Ala Leu Pro Val Thr

```
                  435                 440                 445
Ser Ser Ser Phe Phe Ala Ala Pro Asn Pro Tyr Trp Asn Ser Pro Thr
450                 455                 460
Gly Gly Ile Tyr Pro Asn Thr Arg Leu Pro Thr Ser His Met Pro Ser
465                 470                 475                 480
His Leu Gly Thr Tyr Tyr
                485

<210> SEQ ID NO 4
<211> LENGTH: 480
<212> TYPE: PRT
<213> ORGANISM: HUMAN

<400> SEQUENCE: 4

Met Glu Val Ala Pro Glu Gln Pro Arg Trp Met Ala His Pro Ala Val
1               5                   10                  15

Leu Asn Ala Gln His Pro Asp Ser His His Pro Gly Leu Ala His Asn
                20                  25                  30

Tyr Met Glu Pro Ala Gln Leu Leu Pro Pro Asp Glu Val Asp Val Phe
            35                  40                  45

Phe Asn His Leu Asp Ser Gln Gly Asn Pro Tyr Tyr Ala Asn Pro Ala
        50                  55                  60

His Ala Arg Ala Arg Val Ser Tyr Ser Pro Ala His Ala Arg Leu Thr
65                  70                  75                  80

Gly Gly Gln Met Cys Arg Pro His Leu Leu His Ser Pro Gly Leu Pro
                85                  90                  95

Trp Leu Asp Gly Gly Lys Ala Ala Leu Ser Ala Ala Ala His His
                100                 105                 110

His Asn Pro Trp Thr Val Ser Pro Phe Ser Lys Thr Pro Leu His Pro
            115                 120                 125

Ser Ala Ala Gly Gly Pro Gly Gly Pro Leu Ser Val Tyr Pro Gly Ala
        130                 135                 140

Gly Gly Gly Ser Gly Gly Gly Ser Gly Ser Ser Val Ala Ser Leu Thr
145                 150                 155                 160

Pro Thr Ala Ala His Ser Gly Ser His Leu Phe Gly Phe Pro Pro Thr
                165                 170                 175

Pro Pro Lys Glu Val Ser Pro Asp Pro Ser Thr Thr Gly Ala Ala Ser
            180                 185                 190

Pro Ala Ser Ser Ser Ala Gly Gly Ser Ala Ala Arg Gly Glu Asp Lys
        195                 200                 205

Asp Gly Val Lys Tyr Gln Val Ser Leu Thr Glu Ser Met Lys Met Glu
210                 215                 220

Ser Gly Ser Pro Leu Arg Pro Gly Leu Ala Thr Met Gly Thr Gln Pro
225                 230                 235                 240

Ala Thr His His Pro Ile Pro Thr Tyr Pro Ser Tyr Val Pro Ala Ala
                245                 250                 255

Ala His Asp Tyr Ser Ser Gly Leu Phe His Pro Gly Gly Phe Leu Gly
            260                 265                 270

Gly Pro Ala Ser Ser Phe Thr Pro Lys Gln Arg Ser Lys Ala Arg Ser
        275                 280                 285

Cys Ser Glu Gly Arg Glu Cys Val Asn Cys Gly Ala Thr Ala Thr Pro
        290                 295                 300

Leu Trp Arg Arg Asp Gly Thr Gly His Tyr Leu Cys Asn Ala Cys Gly
305                 310                 315                 320
```

```
Leu Tyr His Lys Met Asn Gly Gln Asn Arg Pro Leu Ile Lys Pro Lys
                325                 330                 335

Arg Arg Leu Ser Ala Ala Arg Arg Ala Gly Thr Cys Cys Ala Asn Cys
            340                 345                 350

Gln Thr Thr Thr Thr Thr Leu Trp Arg Arg Asn Ala Asn Gly Asp Pro
        355                 360                 365

Val Cys Asn Ala Cys Gly Leu Tyr Tyr Lys Leu His Asn Val Asn Arg
    370                 375                 380

Pro Leu Thr Met Lys Lys Glu Gly Ile Gln Thr Arg Asn Arg Lys Met
385                 390                 395                 400

Ser Asn Lys Ser Lys Lys Ser Lys Lys Gly Ala Glu Cys Phe Glu Glu
                405                 410                 415

Leu Ser Lys Cys Met Gln Glu Lys Ser Ser Pro Phe Ser Ala Ala Ala
            420                 425                 430

Leu Ala Gly His Met Ala Pro Val Gly His Leu Pro Pro Phe Ser His
        435                 440                 445

Ser Gly His Ile Leu Pro Thr Pro Thr Pro Ile His Pro Ser Ser Ser
    450                 455                 460

Leu Ser Phe Gly His Pro His Pro Ser Ser Met Val Thr Ala Met Gly
465                 470                 475                 480

<210> SEQ ID NO 5
<211> LENGTH: 422
<212> TYPE: PRT
<213> ORGANISM: HUMAN

<400> SEQUENCE: 5

Met Pro Arg Ser Phe Leu Val Lys Ser Lys Lys Ala His Ser Tyr His
1               5                   10                  15

Gln Pro Arg Ser Pro Gly Pro Asp Tyr Ser Leu Arg Leu Glu Asn Val
                20                  25                  30

Pro Ala Pro Ser Arg Ala Asp Ser Thr Ser Asn Ala Gly Gly Ala Lys
            35                  40                  45

Ala Glu Pro Arg Asp Arg Leu Ser Pro Glu Ser Gln Leu Thr Glu Ala
    50                  55                  60

Pro Asp Arg Ala Ser Ala Ser Pro Asp Ser Cys Glu Gly Ser Val Cys
65                  70                  75                  80

Glu Arg Ser Ser Glu Phe Glu Asp Phe Trp Arg Pro Pro Ser Pro Ser
                85                  90                  95

Ala Ser Pro Ala Ser Glu Lys Ser Met Cys Pro Ser Leu Asp Glu Ala
            100                 105                 110

Gln Pro Phe Pro Leu Pro Phe Lys Pro Tyr Ser Trp Ser Gly Leu Ala
        115                 120                 125

Gly Ser Asp Leu Arg His Leu Val Gln Ser Tyr Arg Pro Cys Gly Ala
    130                 135                 140

Leu Glu Arg Gly Ala Gly Leu Gly Leu Phe Cys Glu Pro Ala Pro Glu
145                 150                 155                 160

Pro Gly His Pro Ala Ala Leu Tyr Gly Pro Lys Arg Ala Ala Gly Gly
                165                 170                 175

Ala Gly Ala Gly Ala Pro Gly Ser Cys Ser Ala Gly Ala Gly Ala Thr
            180                 185                 190

Ala Gly Pro Gly Leu Gly Leu Tyr Gly Asp Phe Gly Ser Ala Ala Ala
        195                 200                 205

Gly Leu Tyr Glu Arg Pro Thr Ala Ala Ala Gly Leu Leu Tyr Pro Glu
    210                 215                 220
```

```
Arg Gly His Gly Leu His Ala Asp Lys Gly Ala Gly Val Lys Val Glu
225                 230                 235                 240

Ser Glu Leu Leu Cys Thr Arg Leu Leu Leu Gly Gly Ser Tyr Lys
            245                 250                 255

Cys Ile Lys Cys Ser Lys Val Phe Ser Thr Pro His Gly Leu Glu Val
        260                 265                 270

His Val Arg Arg Ser His Ser Gly Thr Arg Pro Phe Ala Cys Glu Met
            275                 280                 285

Cys Gly Lys Thr Phe Gly His Ala Val Ser Leu Glu Gln His Lys Ala
        290                 295                 300

Val His Ser Gln Glu Arg Ser Phe Asp Cys Lys Ile Cys Gly Lys Ser
305                 310                 315                 320

Phe Lys Arg Ser Ser Thr Leu Ser Thr His Leu Leu Ile His Ser Asp
            325                 330                 335

Thr Arg Pro Tyr Pro Cys Gln Tyr Cys Gly Lys Arg Phe His Gln Lys
        340                 345                 350

Ser Asp Met Lys Lys His Thr Phe Ile His Thr Gly Glu Lys Pro His
            355                 360                 365

Lys Cys Gln Val Cys Gly Lys Ala Phe Ser Gln Ser Ser Asn Leu Ile
        370                 375                 380

Thr His Ser Arg Lys His Thr Gly Phe Lys Pro Phe Gly Cys Asp Leu
385                 390                 395                 400

Cys Gly Lys Gly Phe Gln Arg Lys Val Asp Leu Arg Arg His Arg Glu
            405                 410                 415

Thr Gln His Gly Leu Lys
            420

<210> SEQ ID NO 6
<211> LENGTH: 331
<212> TYPE: PRT
<213> ORGANISM: HUMAN

<400> SEQUENCE: 6

Met Thr Glu Arg Pro Pro Ser Glu Ala Ala Arg Ser Asp Pro Gln Leu
1               5                   10                  15

Glu Gly Arg Asp Ala Ala Glu Ala Ser Met Ala Pro Pro His Leu Val
            20                  25                  30

Leu Leu Asn Gly Val Ala Lys Glu Thr Ser Arg Ala Ala Ala Ala Glu
        35                  40                  45

Pro Pro Val Ile Glu Leu Gly Ala Arg Gly Gly Pro Gly Gly Gly Pro
    50                  55                  60

Ala Gly Gly Gly Ala Ala Arg Asp Leu Lys Gly Arg Asp Ala Ala
65                  70                  75                  80

Thr Ala Glu Ala Arg His Arg Val Pro Thr Thr Glu Leu Cys Arg Pro
                85                  90                  95

Pro Gly Pro Ala Pro Ala Pro Ala Ser Val Thr Ala Glu Leu
            100                 105                 110

Pro Gly Asp Gly Arg Met Val Gln Leu Ser Pro Ala Leu Ala Ala
        115                 120                 125

Pro Ala Ala Pro Gly Arg Ala Leu Leu Tyr Ser Leu Ser Gln Pro Leu
    130                 135                 140

Ala Ser Leu Gly Ser Gly Phe Phe Gly Glu Pro Asp Ala Phe Pro Met
145                 150                 155                 160

Phe Thr Thr Asn Asn Arg Val Lys Arg Arg Pro Ser Pro Tyr Glu Met
```

```
                    165                 170                 175
Glu Ile Thr Asp Gly Pro His Thr Lys Val Val Arg Arg Ile Phe Thr
                180                 185                 190

Asn Ser Arg Glu Arg Trp Arg Gln Gln Asn Val Asn Gly Ala Phe Ala
            195                 200                 205

Glu Leu Arg Lys Leu Ile Pro Thr His Pro Pro Asp Lys Lys Leu Ser
        210                 215                 220

Lys Asn Glu Ile Leu Arg Leu Ala Met Lys Tyr Ile Asn Phe Leu Ala
225                 230                 235                 240

Lys Leu Leu Asn Asp Gln Glu Glu Gly Thr Gln Arg Ala Lys Thr
                245                 250                 255

Gly Lys Asp Pro Val Val Gly Ala Gly Gly Gly Gly Gly Gly
                260                 265                 270

Gly Gly Ala Pro Pro Asp Asp Leu Leu Gln Asp Val Leu Ser Pro Asn
                275                 280                 285

Ser Ser Cys Gly Ser Ser Leu Asp Gly Ala Ala Ser Pro Asp Ser Tyr
        290                 295                 300

Thr Glu Glu Pro Ala Pro Lys His Thr Ala Arg Ser Leu His Pro Ala
305                 310                 315                 320

Met Leu Pro Ala Ala Asp Gly Ala Gly Pro Arg
                325                 330

<210> SEQ ID NO 7
<211> LENGTH: 158
<212> TYPE: PRT
<213> ORGANISM: HUMAN

<400> SEQUENCE: 7

Met Ser Ser Ala Ile Glu Arg Lys Ser Leu Asp Pro Ser Glu Glu Pro
1               5                   10                  15

Val Asp Glu Val Leu Gln Ile Pro Pro Ser Leu Leu Thr Cys Gly Gly
                20                  25                  30

Cys Gln Gln Asn Ile Gly Asp Arg Tyr Phe Leu Lys Ala Ile Asp Gln
            35                  40                  45

Tyr Trp His Glu Asp Cys Leu Ser Cys Asp Leu Cys Gly Cys Arg Leu
        50                  55                  60

Gly Glu Val Gly Arg Arg Leu Tyr Tyr Lys Leu Gly Arg Lys Leu Cys
65                  70                  75                  80

Arg Arg Asp Tyr Leu Arg Leu Phe Gly Gln Asp Gly Leu Cys Ala Ser
                85                  90                  95

Cys Asp Lys Arg Ile Arg Ala Tyr Glu Met Thr Met Arg Val Lys Asp
            100                 105                 110

Lys Val Tyr His Leu Glu Cys Phe Lys Cys Ala Ala Cys Gln Lys His
        115                 120                 125

Phe Cys Val Gly Asp Arg Tyr Leu Leu Ile Asn Ser Asp Ile Val Cys
        130                 135                 140

Glu Gln Asp Ile Tyr Glu Trp Thr Lys Ile Asn Gly Met Ile
145                 150                 155

<210> SEQ ID NO 8
<211> LENGTH: 11
<212> TYPE: PRT
<213> ORGANISM: ARTIFICIAL SEQUENCE
<220> FEATURE:
<223> OTHER INFORMATION: Synthetic

<400> SEQUENCE: 8
```

```
Tyr Gly Arg Lys Lys Arg Arg Gln Arg Arg
1               5                   10
```

<210> SEQ ID NO 9
<211> LENGTH: 8
<212> TYPE: PRT
<213> ORGANISM: ARTIFICIAL SEQUENCE
<220> FEATURE:
<223> OTHER INFORMATION: SYNTHETIC

<400> SEQUENCE: 9

```
Arg Lys Lys Arg Arg Gln Arg Arg
1               5
```

<210> SEQ ID NO 10
<211> LENGTH: 11
<212> TYPE: PRT
<213> ORGANISM: ARTIFICIAL SEQUENCE
<220> FEATURE:
<223> OTHER INFORMATION: SYNTHETIC

<400> SEQUENCE: 10

```
Tyr Ala Arg Ala Ala Ala Arg Gln Ala Arg Ala
1               5                   10
```

<210> SEQ ID NO 11
<211> LENGTH: 11
<212> TYPE: PRT
<213> ORGANISM: ARTIFICIAL SEQUENCE
<220> FEATURE:
<223> OTHER INFORMATION: SYNTHETIC

<400> SEQUENCE: 11

```
Thr His Arg Leu Pro Arg Arg Arg Arg Arg
1               5                   10
```

<210> SEQ ID NO 12
<211> LENGTH: 11
<212> TYPE: PRT
<213> ORGANISM: ARTIFICIAL SEQUENCE
<220> FEATURE:
<223> OTHER INFORMATION: SYNTHETIC

<400> SEQUENCE: 12

```
Gly Gly Arg Arg Ala Arg Arg Arg Arg Arg
1               5                   10
```

<210> SEQ ID NO 13
<211> LENGTH: 148
<212> TYPE: PRT
<213> ORGANISM: herpes simplex virus 7

<400> SEQUENCE: 13

```
Thr Lys Thr Leu Met Lys Lys Asp Lys Tyr Thr Leu Pro Gly Gly Leu
1               5                   10                  15

Leu Ala Pro Gly Gly Asn Ser Met Ala Ser Gly Val Gly Val Gly Ala
                20                  25                  30

Gly Leu Gly Ala Gly Val Asn Gln Arg Met Asp Ser Tyr Ala His Met
            35                  40                  45

Asn Gly Trp Ser Asn Gly Ser Tyr Ser Met Met Gln Asp Gln Leu Gly
        50                  55                  60

Tyr Pro Gln His Ser Thr Thr Ala Pro Ile Thr Asp Val Ser Leu Gly
65                  70                  75                  80
```

```
Asp Glu Leu Arg Leu Asp Gly Glu Glu Val Asp Met Thr Pro Ala Asp
                85              90              95

Ala Leu Asp Asp Phe Asp Leu Glu Met Leu Gly Asp Val Glu Ser Pro
            100             105             110

Ser Pro Gly Met Thr His Asp Pro Val Ser Tyr Gly Ala Leu Asp Val
            115             120             125

Asp Asp Phe Glu Phe Glu Gln Met Phe Thr Asp Ala Leu Gly Ile Asp
    130             135             140

Asp Phe Gly Gly
145
```